United States Patent

Khan et al.

[11] Patent Number: 5,770,716
[45] Date of Patent: Jun. 23, 1998

[54] SUBSTITUTED PROPARGYLETHOXYAMIDO NUCLEOSIDES, OLIGONUCLEOTIDES AND METHODS FOR USING SAME

[75] Inventors: Shaheer H. Khan, Foster City; Steven M. Menchen, Fremont; Barnett B. Rosenblum, San Jose, all of Calif.

[73] Assignee: The Perkin-Elmer Corporation, Foster City, Calif.

[21] Appl. No.: 833,855

[22] Filed: Apr. 10, 1997

[51] Int. Cl.[6] ............................. C07H 21/02; C12P 19/34
[52] U.S. Cl. .................... 536/23.1; 536/22.1; 536/24.33; 536/25.3; 536/25.32; 536/25.33; 536/25.34; 536/26.26; 536/26.6; 536/26.8; 536/27.14; 536/27.21; 536/27.6; 536/27.8; 536/27.81; 536/28.1; 536/28.2; 536/28.5; 536/28.53; 536/28.54; 435/87; 435/88; 435/89; 435/91.1
[58] Field of Search ................................... 514/45, 46, 47, 514/49, 50, 51; 536/22.1, 23.1, 24.33, 25.3, 25.32, 25.33, 25.34, 26.26, 26.6, 26.8, 27.14, 27.21, 27.6, 27.8, 27.81, 28.1, 28.2, 28.5, 28.53, 28.54; 435/87, 88, 89, 91.1

[56] References Cited

U.S. PATENT DOCUMENTS 5,047,518  9/1991  Hobbs, Jr. et al. .
5,151,507  9/1992  Hobbs, Jr. et al. .

*Primary Examiner*—James O. Wilson
*Attorney, Agent, or Firm*—Paul D. Grossman; The Perkin-Elmer Corporation

[57] ABSTRACT

Substituted propargylethoxyamido nucleosides are disclosed having the structure

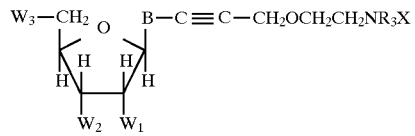

wherein X is selected from the group consisting of amino alkanoic acid, alkylamino benzoic acid, α-amino acid, and 4-amino-2-butynoic acid. $R_1$ and $R_2$ taken separately are selected from the group consisting of —H, lower alkyl, protecting group, and label; $R_3$ is selected from the group consisting of —H and lower alkyl. B is a 7-deazapurine, purine, or pyrimidine nucleoside base. When B is purine or 7-deazapurine, the sugar moiety is attached at the $N^9$-position of the purine or deazapurine, and when B is pyrimidine, the sugar moiety is attached at the $N^1$-position of the pyrimidine. When B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine. $W_1$ is selected from the group consisting of —H and —OH. $W_2$ is —OH or a moiety which renders the nucleoside incapable of forming a phosphodiester bond at the 3'-position. $W_3$ is selected from the group consisting of —$PO_4$, —$P_2O_7$, —$P_3O_{10}$, phosphate analog, and —OH. Additionally, a primer extension method is provided employing the above X-substituted propargylethoxyamido nucleosides, and polynucleotides including the above X-substituted propargylethoxyamido nucleosides is provided.

12 Claims, 14 Drawing Sheets

6-FAM-ddATP 1 pm

Dye Terminator

Dye Primer

6-FAM-ddATP 4 pm

Dye Terminator

Dye Primer

6-FAM-ddATP 150 pm

Terminator Dye

Primer Dye ddCTP-EO-HEX-I, 50 pm ddCTP-EO-BN-HEX-I, 25 pm ddCTP-EO-GLY-HEX-I, 250 pm

SUBSTITUTED PROPARGYLETHOXYAMIDO NUCLEOSIDES, OLIGONUCLEOTIDES AND METHODS FOR USING SAME

FIELD OF THE INVENTION

This invention relates generally to nucleotide compounds useful as substrates for polymerase enzymes, methods for using such nucleotide compounds in a primer extension reaction, and polynucleotides including such nucleotide compounds.

REFERENCES

[F]DNTP Reagents Protocol, PE Applied Biosystems, Revision A, p/n 402774 (March 1996)

ABI PRISM™ 373DNA Sequencing System User's Manual, p/n903204 (June, 1994)

ABI PRISM™ Dye Primer Cycle Sequencing Core Kit with AmpliTaq® DNA Polymerase, FS, Protocol, Revision C, p/n 402114 (1996)

ABI PRISM™ Dye Terminator Cycle Sequencing Core Kit Protocol, PE Applied Biosystems, Revision A, p/n 402116 (August 1995)

Benson et al., U.S. patent application Ser. No. 08/626,085 filed Apr. 1, 1996

Bergot, et al., U.S. Pat. No. 5,366,860 (1994)

Connell et al., Biotechniques, 5(4): 342–348 (1987)

Eckstein ed., Oligonucleotides and Analogs, Chapters 8 and 9, IRL Press (1991)

Eckstein et al., Nucleic Acids Research, 16(21): 9947–59 (1988)

Gish et al, Science, 240: 1520 (1988)

Hermanson, Bioconjugate Techniques, Academic Press (1996)

Hobbs, et al., U.S. Pat. No. 5,151,507 (1992)

Kasai, et al., Anal. Chem., 47: 34037 (1975)

Khanna, et al., U.S. Pat. No. 4,318,846 (1988)

Lee et al, Nucleic Acids Research, 20(10): 2471–2483 (1992)

Menchen et al, U.S. Pat. No. 5,188,934 (1993)

Murray, Nucleic Acids Research, 17(21): 8889 (1989)

Prober et al., Science, 238: 336–341 (1987)

Sanger, et al., Proc. Natl. Acad. Sci., 74: 5463–5467 (1977)

Scheit, Nucleotide Analogs, John Wiley (1980)

Shaw et al., Nucleic Acids Research, 23: 4495–4501 (1995).

Smith et al., U.S. Pat. No. 5,171,534 (1992)

Stryer, Biochemistry, W. H. Freeman (1981)

Trainor, Anal. Chem., 62: 418–426 (1990)

BACKGROUND

Nucleic acid sequencing has become a vitally important technique in modem biology and biotechnology, providing information relevant to fields ranging from basic biological research to drug discovery to clinical medicine. Because of the large volume of DNA sequence data to be collected, automated techniques have been developed to increase the throughput and decrease the cost of nucleic acid sequencing methods (Smith; Connell; Trainor).

A preferred automated nucleic acid sequencing method is based on the enzymatic replication technique developed by Sanger (Sanger). In Sanger's technique, the sequence of a single-stranded template nucleic acid is determined using a nucleic acid polymerase to synthesize a set of polynucleotide fragments wherein the fragments (i) have a sequence complementary to the template sequence, (ii) vary in length by a single nucleotide, and (iii) have a 5'-end terminating in a known nucleotide, e.g., A, C, G, or T. In the method, an oligonucleotide primer is annealed to a 3'-end of a template nucleic acid to be sequenced, the 3'-end of the primer serving as the initiation site for polymerase-mediated polymerization of a complementary polynucleotide fragment. The enzymatic polymerization step is carried out by combining the template-primer hybrid with the four natural deoxynucleotides ("dNTPs"), a nucleic acid polymerase enzyme, and a 2',3'-dideoxynucleotide triphosphate ("ddNTP") "terminator". The incorporation of the terminator forms a fragment which lacks a hydroxy group at the 3'-terminus and thus can not be further extended by the polymerase, i.e., the fragment is "terminated". The competition between the ddNTP and its corresponding dNTP for incorporation results in a distribution of different-sized fragments, each fragment terminating with the particular terminator used in the reaction. To discover the complete sequence of the template nucleic acid, four parallel reactions are run, each reaction using a different ddNTP terminator. To determine the size distribution of the fragments, the fragments are separated by electrophoresis such that fragments differing in size by a single nucleotide are resolved.

In a modem variant of the classical Sanger technique, the nucleotide terminators are labeled with fluorescent dyes (Prober; Hobbs), and a thermostable DNA polymerase enzyme is used (Murray). Several advantages are realized by utilizing dye-labeled terminators: (i) problems associated with the storage, use and disposal of radioactive isotopes are eliminated; (ii) the requirement to synthesize dye-labeled primers is eliminated; and, (iii) when using a different dye label for each A,G,C, or T nucleotide, all four reactions can be performed simultaneously in a single tube. Using a thermostable polymerase enzyme (i) permits the polymerization reaction to be run at elevated temperature thereby disrupting any secondary structure of the template resulting in fewer sequence-dependent artifacts, and (ii) permits the sequencing reaction to be thermocycled, thereby serving to linearly amplify the amount of extension product produced, thus reducing the amount of DNA template required to obtain a sequence.

While these modem variants on Sanger sequencing methods have proven effective, several problems remain with respect to optimizing their performance and economy. One problem encountered when using presently available dye-labeled terminators in combination with thermostable polymerase enzymes in a Sanger-type nucleic acid sequencing process, particularly in the case of fluorescein-type dye labels, is that a large excess of dye-labeled terminator over the unlabeled dNTPs is required, up to a ratio of 50:1. This large excess of labeled terminator makes it necessary to purify the sequencing reaction products prior to performing the electrophoretic separation step. This clean-up step is required in order to avoid interference caused by the configuration of unincorporated labeled terminator species and bona fide sequencing fragments. A typical clean-up method includes an ethanol precipitation or a chromatographic separation (ABI PRISM™ Dye Terminator Cycle Sequencing Core Kit Protocol). Such a clean-up step greatly complicates the task of developing totally automated sequencing systems wherein the sequencing reaction products are transferred directly into an electrophoretic separation process.

A second problem encountered when using presently available dye-labeled terminators in combination with a thermostable polymerase in a Sanger-type nucleic acid sequencing process is that an uneven distribution of peak heights is obtained when the reaction products are separated by electrophoresis and detected using fluorescence detection. Such uneven peak heights are disadvantageous because they make automated sequence determination and heterozygote detection substantially less reliable.

SUMMARY

The present invention is directed towards our discovery of a novel class of substituted propargylethoxyamido nucleosides useful as chain-terminating nucleotides, and, as chain-extending nucleotides, in a primer extension reaction, e.g., in a Sanger-type DNA sequencing reaction or in a PCR reaction.

It is an object of the invention to provide a nucleotide which can be used to form a labeled chain-terminating nucleotide.

It is a further object of the invention to provide a chain-terminating nucleotide which includes a label.

It is yet an additional object of the invention to provide a chain-terminating nucleotide which includes a fluorescent label wherein a reduced excess concentration of such labeled chain-terminating nucleotide over an unlabeled chain-terminating nucleotide is required in a Sanger-type DNA sequencing process.

It is another object of the invention to provide a labeled chain-terminating nucleotide which results in a more even distribution of peak heights in a Sanger-type DNA sequencing process.

It is an object of the invention to provide a nucleotide which can be used to form a labeled chain-extending nucleotide.

It is a further object of the invention to provide a chain-extending nucleotide which includes a label.

It is another object of the invention to provide labeled polynucleotides.

It is an additional object of the invention to provide methods including a primer extension reaction utilizing the substituted propargylethoxyamido nucleotides of the invention.

In a first aspect, the foregoing and other objects of the invention are achieved by a nucleoside compound having the structure:

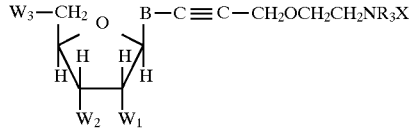

wherein X is selected from the group consisting of

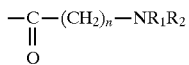

where n ranges from 1 to 5,

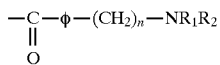

where n ranges from 1 to

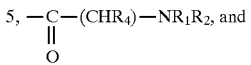

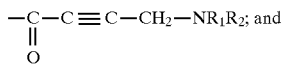

$R_1$ and $R_2$ taken separately are selected from the group consisting of —H, lower alkyl, protecting group, and label. $R_3$ is selected from the group consisting of —H and lower alkyl. B is a 7-deazapurine, purine, or pyrimidine nucleoside base, where, when B is purine or 7-deazapurine, the sugar moiety is attached at the $N^9$-position of the purine or deazapurine, and when B is pyrimidine, the sugar moiety is attached at the $N^1$-position of the pyrimidine, and when B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine. $W_1$ is selected from the group consisting of —H and —OH; $W_2$ is —OH or a moiety which renders the nucleoside incapable of forming a phosphodiester bond at the 3'-position; and $W_3$ is selected from the group consisting of —$PO_4$, —$P_2O_7$, —$P_3O_{10}$, phosphate analog, and —OH.

In a first preferred embodiment of the first aspect of the invention, one of $R_1$ and $R_2$ is label, and more preferably, the label is a fluorescein-type dye, a rhodamine-type dye or a FLAN-type dye.

In a second preferred embodiment of the first aspect of the invention, $W_1$ is —H; $W_2$ is —OH or a moiety which renders the nucleoside incapable of forming a phosphodiester bond at the 3'-position; and $W_3$ is —$P_3O_{10}$. More preferably, $W_2$ selected from the group consisting of —OH, —H, azido, amino, fluro, and methoxy.

In a third preferred embodiment of the first aspect of the invention, B is selected from the group consisting of uracil, cytosine, 7-deazaadenine, and 7-deazaguanosine.

In a fourth preferred embodiment of the first aspect of the invention, X is

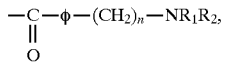

n=1 and the φ-group is in a para configuration.

In a second aspect, the foregoing and other objects of the invention are achieved by a method for performing a primer extension reaction comprising the steps of providing a template nucleic acid; annealing an oligonucleotide primer to a portion of the template nucleic acid; and adding primer-extension reagents to the primer-template hybrid for extending the primer, the primer extension reagents including a nucleoside compound of the first aspect of the invention as described above.

In a third aspect, the foregoing and other objects of the invention are achieved by a polynucleotide including a nucleoside compound of the first aspect of the invention as described above.

DETAILED DESCRIPTION OF THE PREFERRED EMBODIMENTS

Figure 1A:
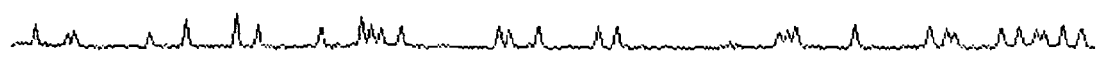
FIG. 1A shows results from a Terminator Titration Assay using 1 pmol of a 6-FAM-ddATP terminator.
Figure 1A:
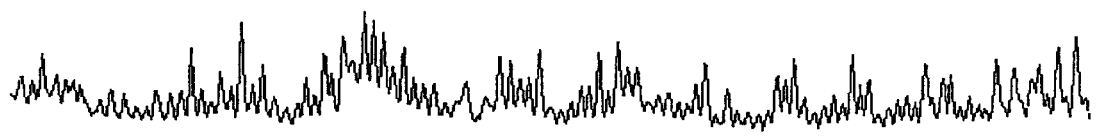

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises a novel class of substituted propargylethoxyamido nucleoside compounds useful as substrates for polymerase enzymes, polynucleotides including such nucleoside compounds, and methods for using such nucleoside compounds in a primer extension reaction. The compounds of the present invention find particular application in the preparation of dye labeled nucleotide chain-terminating agents for use in Sanger-type DNA sequencing methods, and, in the preparation of dye labeled nucleotide chain-extending agents for use in methods including a primer extension reaction, e.g., PCR.

The invention is based in part on the discovery that the subject substituted propargylethoxyamido nucleotides are particularly good substrates for thermostable DNA polymerase enzymes, i.e., (i) a significantly reduced molar excess is required in a Sanger-type DNA sequencing reaction relative to that required when using currently available labeled terminators, and, (ii) a more even distribution of peak heights is seen in a Sanger-type DNA sequencing process relative to that seen when using currently available labeled terminators.

I. DEFINITIONS

Unless stated otherwise, the following terms and phrases as used herein are intended to have the following meanings:

The term "lower alkyl" denotes straight-chain and branched hydrocarbon moieties containing from 1 to 8 carbon atoms, i.e., methyl, ethyl, propyl, isopropyl, tert-butyl, isobutyl, sec-butyl, neopentyl, tert-pentyl, and the like.

The term "label" refers to a moiety that, when attached to the nucleosides of the invention, render such nucleosides, and polynucleotides containing such nucleotides, detectable using known detection means. Exemplary labels include fluorophores, chromophores, radioisotopes, spin-labels, enzyme labels, chemiluminescent labels, and the like, which allow direct detection of a labeled compound by a suitable detector, or, a ligand, such as an antigen, or biotin, which can bind specifically with high affinity to a detectable anti-ligand, such as a labeled antibody or avidin. Preferably the labels are fluorescent dyes such as fluorescein-type or rhodamine-type dyes (Lee; Menchen).

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms (Stryer). The term "nucleotide" as used herein refers to a phosphate ester of a nucleoside, e.g., triphosphate esters, wherein the most common site of esterification is the hydroxyl group attached at the C-5 position of the pentose. Many times in the present disclosure the term nucleoside will be intended to include both nucleosides and nucleotides. "Analogs" in reference to nucleosides include synthetic analogs having modified base moieties, modified sugar moieties, and/or modified phosphate ester moieties, e.g., as described elsewhere (Scheit; Eckstein 1991).

As used herein, the terms "polynucleotide" or "oligonucleotide" refer to linear polymers of natural nucleotide monomers or analogs thereof, including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., H, $NH_4$, Na, and the like if such counterions are present. Polynucleotides typically range in size from a few monomeric units, e.g. 8–40, to several thousands of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

The term "phosphate analog" refers to analogs of phosphate wherein the phosphorous atom is in the +5 oxidation state and one or more of the oxygen atoms is replaced with a non-oxygen moiety, exemplary analogs including phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present.

As used herein, the term "propargylamido linker" shall refer to a linker having the structure

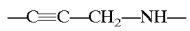

and the term "propargylethoxyamido linker" shall refer to a linker having the structure

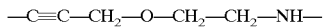

where, for each of the above structures, the terminal end of the acetylene is bound to a nucleotide base, and the amide nitrogen is bound through a convenient linkage to a label.

In reference to the moiety "X" of the present invention, the term "amino alkanoic acid" shall refer to the structure

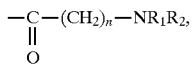

where n ranges from 1 to 5, the term "alkylamino benzoic acid" shall refer to the structure

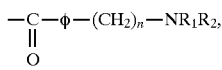

where n ranges from 1 to 5, the term "α-amino acid" shall refer to the structure

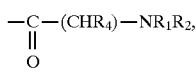

and the term "4-amino-2-butynoic acid" shall refer to the structure

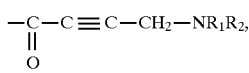

where in the above structures $R_1$ and $R_2$ taken separately are —H lower alkyl, protecting group, or label, and $R_4$ is an amino acid side chain, either natural (Stryer) or synthetic.

The term "propargylethoxyamido nucleotide" refers to a nucleotide including a propargylethoxyamido linker attached to a nucleobase of a nucleotide.

The term "fluorescein-type dye" refers to a class of xanthene dye molecules which include the following fused three-ring system:

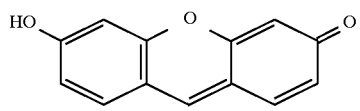

where a wide variety of substitutions are possible at each deoxy ring position. A particularly preferred subset of fluorescein-type dyes include the 4,7,-dichorofluoresceins (Menchen). Examples of fluorescein-type dyes used as fluorescent labels in DNA sequencing methods include 6-carboxyfluorescein (6-FAM), 5-carboxyfluorescein (5-FAM), 6-carboxy-4,7,2',7'-tetrachlorofluorescein (TET), 6-carboxy-4,7,2',4',5',7'-hexachlorofluorescein (HEX), 5-(and 6)carboxy-4',5'-dichloro-2'7'-dimethoxyfluorescein (JOE), and 5-carboxy-2',4',5',7'-tetrachlorofluorescein (ZOE). Many times the designation –1 or –2 is placed after an abbreviation of a particular dye, e.g., HEX-1. The "–1" and "–2" designations indicate the particular dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1M triethylammonium acetate to 35% acetonitrile/65% 0.1 M triethylammonium acetate.

The term "rhodamine-type dye" refers to a class of xanthene dye molecules which include the following fused three-ring system:

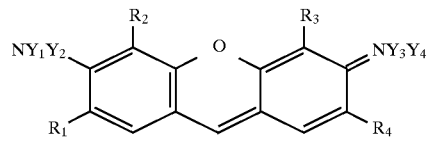

where preferably $Y_1$–$Y_4$ taken separately are hydrogen or lower alkyl, or, when taken together, $Y_1$ and $R_2$ is propano and $Y_2$ and $R_1$ is propano, or, when taken together, $Y_3$ and $R_3$ is propano and $Y_4$ and $R_4$ is propano. A wide variety of substitutions are possible at each deoxy ring position including the $R_1$–$R_4$ positions. Exemplary rhodamine type dyes useful as nucleoside labels include tetramethylrhodamine (TAMRA), 4,7-diclorotetramethyl rhodamine (DTAMRA), rhodamine X (ROX), rhodamine 6G (R6G), rhodamine 110 (R110), and the like (Bergot; Lee).

As used herein, the term "FLAN dye" refers to asymmetric benzoxanthene dye compounds having the formula:

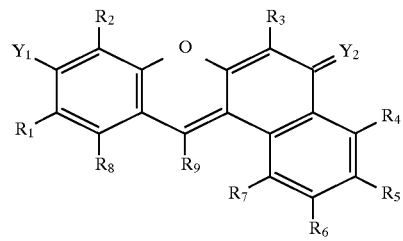

wherein $Y_1$ and $Y_2$ taken separately are hydroxyl, oxygen, imminium, or amine. $R_1$–$R_4$ taken separately are hydrogen, fluorine, chlorine, lower alkyl, lower alkene, lower alkyne, sulfonate, amino, ammonium, amido, nitrile, alkoxy, linking group, or combinations thereof And, $R_9$ is acetylene, alkane, alkene, cyano, substituted phenyl, or combinations thereof, the substituted phenyl having the structure:

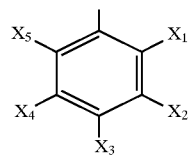

wherein $X_1$ is carboxylic acid or sulfonic acid; $X_2$ and $X_5$ taken separately are hydrogen, chlorine, fluorine, or lower alkyl; and $X_3$ and X4 taken separately are hydrogen, chlorine, fluorine, lower alkyl, carboxylic acid, sulfonic acid, or linking group (Benson).

As used herein the term "primer-extension reagent" means a reagent including components necessary to effect the enzymatic template-mediated extension of an oligonucleotide primer. Primer extension reagents include: (i) a polymerase enzyme, e.g., a thermostable polymerase enzyme such as Taq polymerase; (ii) a buffer; (iii) chain-extension nucleotides, e.g., a deoxynucleotide triphosphate, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of Sanger-type DNA sequencing reactions, (iv) one or more chain-terminating nucleotides, e.g., dideoxynucleotide triphosphates, e.g., dideoxyguanosine 5'-triphosphate, 7-deazadideoxyguanosine 5'-triphosphate, dideoxyadenosine 5'-triphosphate, dideoxythymidine 5'-triphosphate, and dideoxycytidine 5'-triphosphate.

"Template nucleic acid" refers to any nucleic acid which can be presented in a single stranded form and is capable of annealing with a primer oligonucleotide. Exemplary template nucleic acids include DNA, RNA, which DNA or RNA may be single stranded or double stranded. More particularly, template nucleic acid may be genomic DNA, messenger RNA, cDNA, DNA amplification products from a PCR reaction, and the like. Methods for preparation of template DNA may be found elsewhere (ABI PRISM™ Dye Primer Cycle Sequencing Core Kit).

II. SUBSTITUTED PROPARGYLETHOXYAMIDO NUCLEOTIDE COMPOUNDS

In a first aspect, the present invention comprises a novel class of substituted-propargylethoxyamido nucleotide compounds having the general structure shown immediately below as Formula I. (Note that all molecular structures provided throughout this disclosure are intended to encompass not only the exact electronic structure presented, but also include all resonant structures and protonation states thereof.)

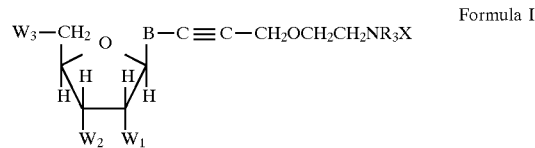

Formula I

In the structure of Formula I, B is a 7-deazapurine, purine, or pyrimidine nucleotide base, where in a preferred embodiment, B is chosen from the group consisting of uracil, cytosine, 7-deazaadenine, and 7-deazaguanosine. When B is purine or 7-deazapurine, the sugar moiety of the nucleotide is attached at the $N^9$-position of the purine or deazapurine, and when B is pyrimidine, the sugar moiety is attached at the $N^1$-position of the pyrimidine. When B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine.

$W_1$ is selected from among —H and —OH. When $W_1$ is —OH the nucleoside is a ribonucleotide, and when $W_1$ is —H the nucleoside is a deoxyribonucleotide.

$W_2$ is —OH or a moiety which renders the nucleoside incapable of forming a phosphodiester bond at the 3'-position. Preferred moieties useful for this function include —H, azido, amino, halo, methoxy, and the like. In a particularly preferred embodiment, $W_2$ is —H or fluoro.

$W_3$ is selected from the group consisting of —$PO_4$, —$P_2O_7$, —$P_3O_{10}$, phosphate analog, and —OH. In a preferred embodiment useful for enzymatic synthesis of polynucleotides, $W_3$ is —$P_3O_{10}$.

X is selected from the group consisting of amino alkanoic acid, alkylamino benzoic acid, α-amino acid, and 4-amino-2-butynoic acid. Preferably, X is alkylamino benzoic acid. When X is amino alkanoic acid or alkylamino benzoic acid, n ranges from 1 to 5, and more preferably, n ranges from 1 to 3. When X is alkylamino benzoic acid, the phenyl group may be in a meta, para, or ortho configuration with respect to the neighboring carbonyl and methylene groups. In a preferred embodiment, the phenyl group is in a para configuration. When X is α-amino acid, the amino acid side chain may be any suitable natural or synthetic amino acid side chain.

For any of the above-described X moieties, $R_1$ and $R_2$ are chosen from among —H lower alkyl, protecting group, or label. Preferably, the label is a fluorescent dye. More preferably the label is a fluorescein-type fluorescent dye, a rhodamine-type fluorescent dye or a FLAN-type fluorescent dye. Preferably, when one of $R_1$ and $R_2$ is a label, the other is either —H or lower alkyl. Preferred protecting groups include haloacetyl, acyl, alkoxycarbonyl, or sulfonyl. More preferably, the protecting group is trifluoroacetyl.

The label is attached to the nucleoside through a "linkage" typically formed by the reaction of the primary or secondary amino moiety of the substituted propargylethoxyamido nucleoside with a "complementary functionality" located on the label. Preferably, the complementary functionality is isothiocyanate, isocyanate, acyl azide, N-hydroxysuccinimide (NHS) ester, sulfonyl chloride, aldehyde or glyoxal, epoxide, carbonate, aryl halide, imidoester, carbodiimide, anhydride, 4,6-dichlorotriazinylamine, or other active carboxylate (Hermanson). In a particularly preferred embodiment, the complementary functionality is an activated NHS ester which reacts with the amine of the substituted propargylethoxyamido nucleoside of the invention, where to form the activated NHS ester, a label including a carboxylate complementary functionality is reacted with dicyclohexylcarbodiimide and N-hydroxysuccinimide to form the NHS ester (Khanna; Kasai). Table 1 below shows a sampling of representative complementary functionalities and resulting linkages formed by reaction of the complementary functionality with the amine of the substituted propargylethoxyamido nucleoside.

TABLE 1

| Complementary Functionality | Linkage |
|---|---|
| —NCS | —NHCSNH— |
| ![structure with Cl, N, Cl] —NH-triazine-Cl | ![structure with Cl, N, NH] —NH-triazine-NH— |
| —$SO_2X$ | —$SO_2NH$— |
| —C(=O)—O—N(succinimide) | —C(=O)—NH— |

$R_3$ is selected from the group consisting of —H and lower alkyl.

III. SYNTHESIS OF SUBSTITUTED PROPARGYLETHOXYAMIDO NUCLEOTIDES AND LABELED NUCLEOTIDES

FIGS. 2–9 show an exemplary synthesis of several of the substituted propargylethoxyamido nucleosides of the invention. In the synthesis, a bromoethanol 1 is reacted with a potassium phthalimide 2 to give a phthalimido derivative 3. The phthalimido derivative is then O-alkylated with propargyl bromide 4 in the presence of NaH, resulting in a protected 3-(2-phthalimidoethoxy)propyne linking arm 5. See FIG. 2. An iodo-nucleoside 6 is then reacted with the protected linking arm in the presence of cuprous iodide, tetrakis(triphenylphosphine)palladium, and triethylamine in dimethylformamide for approximately 12 hours at ambient temperature or until the reaction is complete as determined by TLC thereby forming compound 7. The solution is then concentrated in vacuo and the product is purified by silica gel flash chromatography and is analyzed for identity and purity by proton NMR and analytical reverse-phase HPLC. Treatment with ethylenediamine, followed by acetylation with ethyl trifluoroacetate, gives a nucleoside-linking arm compound 8. See FIG. 3. Freshly distilled phosphorous oxychloride is added to the nucleoside-linking arm compound 8 in trimethylphosphate at $-30°$ C. to form the corresponding dichloromonophosphate 9. The reaction mixture is quenched with 2M tetraethylammonium bicarbonate (TEAB) pH 8.0 to yield a monophosphate 10, which is then purified by preparative reverse-phase HPLC. See FIG. 4. The monophosphate 10 is activated with carbonyldiimidazole (CDI) and excess CDI is quenched with MeOH to yield an activated monophosphate 11. The activated monophosphate is reacted, at room temperature, with tributylammonium pyrophosphate. When complete, the reaction is quenched with 0.2M TEAB and purified by reverse phase HPLC giving the protected triphosphate 12. The purified protected triphosphate is evaporated to dryness and resuspended in concentrated aqueous NH4OH to remove the TFA group giving the propargylethoxyamido nucleotide 13. See FIG. 5.

Generally, attachment of a X moiety to a propargylethoxyamido nucleotide, e.g., 13, is performed as follows. To protect an amine functionality of the X moiety, an amine-protected X moiety is formed by reacting the X moiety with an amine protecting agent, e.g., trifluoroacetate, e.g., FIGS. 6A–C compounds 14, 17, or 20. To activate an acid functionality of the amine-protected X moiety, the amine-protected X moiety is reacted with an acid activating agent, e.g., N-hydroxysuccinimide, e.g., see e.g., FIGS. 6A–C compounds 15, 18, or 21. Next, the amine-protected acid-activated X moiety is reacted with a propargylethoxyamido nucleotide, e.g., 13, under basic conditions, e.g., 250 mM bicarbonate buffer, pH 9, to yield an amine-protected substituted propargylethoxyamido nucleotide, e.g., see FIG. 7 compound 22, FIG. 8 compound 24, or FIG. 9 compound 26. Finally, the amine protecting group is removed from the amine-protected substituted propargylethoxyamido nucleotide by reaction with a strong base, e.g., NH$_4$OH, resulting in a substituted propargylethoxyamido nucleotide, e.g., see FIG. 7 compound 23, FIG. 8 compound 25, or FIG. 9 compound 27.

Generally, in a preferred method, labeled substituted-propargylethoxyamido nucleosides of the invention are prepared as follows. A substituted-propargylethoxyamido nucleoside, e.g., 23, 25, or 27, is dissolved in a neutral buffered solution, e.g., 100 mM TEAB (pH 7.0), the solution is evaporated to dryness, and the nucleoside is resuspended in a basic buffered solution, e.g., 250 mM sodium bicarbonate buffer pH=9. A label-NHS ester (in DMSO) is added to the solution and allowed to react overnight with stirring. When complete, the reaction mixture is purified by ion exchange and reverse phase HPLC yielding a labeled substituted-propargylethoxyamido nucleoside.

IV. METHODS UTILIZING THE PROPARGYLETHOXYAMIDO COMPOUNDS

The propargylethoxyamido compounds of the invention are particularly well suited for use in methods which include a template-mediated primer extension reaction of the type including the following steps: (i) providing a template nucleic acid; (ii) annealing an oligonucleotide primer to a portion of the template nucleic acid thereby forming a primer-template hybrid; and (iii) adding primer-extension reagents to the primer-template hybrid for extending the primer. In particular, the compounds of the invention provide a means for incorporating a label directly into a primer extension product.

In a first preferred class of methods utilizing a primer extension reaction, the extension products are labeled by including labeled substituted propargylethoxyamido nucleotides of the invention into the primer extension reaction thereby randomly incorporating labels throughout the extension product ([F]dNTP Reagents Protocol). Such a method can be used to label PCR amplicons as well as single-primer derived extension products. To label an extension product in this way, the primer extension reaction is performed using established protocols, but a labeled substituted propargylethoxyamido nucleotides is added to the reaction. Generally, to perform a primer extension reaction in the context of PCR, template nucleic acid is mixed with 20 pmol of each primer and primer-extension reagents comprising 20 mM buffer at pH 8, 1.5 mM MgCl$_2$, 50 mM of each deoxynucleotide triphosphate (dNTP), and 2 units of Taq polymerase or other suitable thermostable polymerase. The reaction mixture is then thermocycled, a typical thermocycle profile comprising a denaturation step (e.g. 96° C., 15 s), a primer annealing step (e.g., 55° C., 30 s), and a primer extension step (e.g., 72° C., 90 s). Typically, the thermocycle is repeated from about 10 to 40 cycles. For PCR amplifications, the typical ratio of labeled deoxynucleotide triphosphate to unlabeled deoxynucleotide triphosphate is between 100:1 to 1000:1, depending on the amount of signal desired. The maximum ratio of labeled deoxynucleotide triphosphate to unlabeled deoxynucleotide triphosphate that can be used in a PCR reaction mixture without adversely affecting amplification efficiency is approximately 1:4.

In a second preferred class of methods utilizing a primer extension reaction, the extension products are labeled by including substituted propargylethoxyamido nucleotides of the invention into the primer extension reaction thereby randomly incorporating detectable labels at the 3'-terminal nucleotide of the extension product, e.g., Sanger-type DNA sequencing. Generally, to perform a primer extension reaction in the context of Sanger-type DNA sequencing using labeled dideoxynucleotide triphosphates of the invention, 1 μl of template solution (1 μl of PCR reaction diluted with 5 μl water) and 2 μl of primer (0.4 pmol/μl) is mixed with primer-extension reagents comprising 2 μl buffer (400 mM Tris-HCl, 10 mM MgCl$_2$, pH 9.0.), 2 μl of a deoxynucleotide/labeled dideoxynucleotide mixture (T-termination reaction, 1250 μM ddTTP, 250 μM dATP, 250 μM dCTP, 180 μM7-deaza-dGTP, and 250 μM dTTP), and 2 μl of polymerase enzyme (5 Units/μl where one unit is defined as in Lawyer). The reaction is then thermocycled using the following exemplary program: denaturation at 98° C. for 5 s followed by repeated cycles of 96° C. for 5 s; 55° C. for 40 s; 68° C. for 1 min, where the cycle is repeated approximately 15 times.

The substituted propargylethoxyamido nucleoside compounds of the invention are also well suited to be used in the context of variants of Sanger-type sequencing methods which rely on base-specific cleavage of the primer extension products, e.g., methods utilizing labile nucleotides (Eckstein 1988; Shaw).

V. EXAMPLES

The invention will be further clarified by a consideration of the following examples, which are intended to be purely exemplary of the invention and not to in any way limit its scope.

EXAMPLE 1

Terminator Titration Assay for Determining the Required Terminator Excess in a Sequencing Reaction A Terminator Titration Assay was used to determine the minimum amount of dye-labeled terminator required to create a full sequencing ladder, i.e., a sequencing ladder including all fragments terminating in a particular base having a length of between about 20 to about 600 nucleotides. The key components of the Terminator Titration Assay were (i) a primer labeled with a first dye, and (ii) a terminator labeled with a second dye spectrally resolvable from the first dye. In the assay, when an insufficient concentration of dye terminator was added to the sequencing reaction, no dideoxy-terminated fragments were formed, and all that was seen on a sequencing gel were products formed by "false stops" that were labeled with the first dye only. As used herein the term "false stop" refers to a primer extension product not terminating in a dideoxy terminator, such product probably being formed when a polymerase enzyme spontaneously disengages from a template nucleic acid strand. When too much terminator was used, only short termination products were formed, i.e., less than about 50 nucleotides in length, such products including both the first and second dyes. When the proper amount of terminator was used, a full sequencing ladder was produced, each fragment of the ladder being labeled with both the first and second dyes.

The dye-terminator reactions were performed using AmpliTaq DNA Polymerase, FS following protocols provided in the ABI PRISM™ Dye Terminator Cycle Sequencing Core Kit Manual (PE Applied Biosystems p/n 402116). (The FS enzyme is a recombinant Thermus aquaticus DNA polymerase having two point mutations—G46D and F667Y). All reagents except the dNTP mix, dye labeled primers, and dye-labeled terminators were from an ABI PRISM™ Dye Terminator Core Kit (PE Applied Biosystems p/n 402117). The dNTP mix consisted of 2 mM each of dATP, dCTP, 7-deaza-dGTP and dTTP. A premix of reaction components was prepared as shown in the following table wherein all quantities are given on a per reaction basis:

| | |
|---|---|
| 5X Buffer | 4.0 μL |
| dNTP mix | 1.0 μL |
| Template:pGEM ®-3Zf(+), 0.2 μg/μL | 5.0 μL |
| Primer: −21 M13 (forward), 0.8 pmol/μL | 4.0 μL |
| AmpliTaq DNA Polymerase, FS | 0.5 μL |
| H$_2$O | 0.5 μL |

Reactions were assembled in 0.5 ml microcentrifuge tubes adapted for the Perkin-Elmer 480 DNA Thermal Cycler (PE Applied Biosystems p/n N801-100). Reaction volumes were 20 μL, including 15 μL of the above reaction premix, a variable amount of dye labeled terminator, and a sufficient volume of water to bring the total reaction volume up to 20 μL. From 1 to 500 pmol of a dye-labeled terminator was added to each reaction. 30 μL of mineral oil was added to the top of each reaction to prevent evaporation. Reactions were thermocycled as follows: 96° C. for 30 sec, 50° C. for 15 sec, and 60° C. for 4 min, for 25 cycles; followed by a 4° C. hold cycle.

All reactions were purified by spin-column purification on Centri-Sep spin columns according to manufacturer's instructions (Princeton Separations p/n CS-901). Gel material in the column was hydrated with 0.8 mL deionized water for at least 30 minutes at room temperature. After the column was hydrated and it was determined that no bubbles were trapped in the gel material, the upper and lower end caps of the column were removed, and the column was allowed to drain by gravity. The column was then inserted into the wash tubes provided in the kit and centrifuged in a variable speed microcentrifuge at 1300×g for 2 minutes, removed from the wash tube, and inserted into a sample collection tube. The reaction mixture was carefully removed from under the oil and loaded onto the gel material. Columns were centrifuged in a variable speed microcentrifuge at 1300×g for 2 minutes. Eluted samples were then dried in a vacuum centrifuge.

Prior to loading onto a sequencing gel, the dried samples were resuspended in 25 μL of Template Suppression Reagent (PE Applied Biosystems p/n 401674), vortexed, heated to 95° C. for 2 minutes, cooled on ice, vortexed again, and centrifuged (13,000×g). 10 μL of the resuspended sample was aliquoted into sample vials (PE Applied Biosystems p/n 401957) adapted for the PE ABI PRISM™ 310 Genetic Analyzer (PE Applied Biosystems p/n 310-00-100/120). Electrophoresis on the 310 Genetic Analyzer was performed with a sieving polymer and a capillary specially adapted for DNA sequencing analysis (PE Applied Biosystems p/n 402837 (polymer) and p/n 402840 (capillary)). In each case, the sieving polymer included nucleic acid denaturants. Samples were electrokinetically injected onto the capillary for 30 sec at 2.5 kV, and run for 2 hr at 12.2 kV with the outside wall of the capillary maintained at 50° C.

Figure 1B:
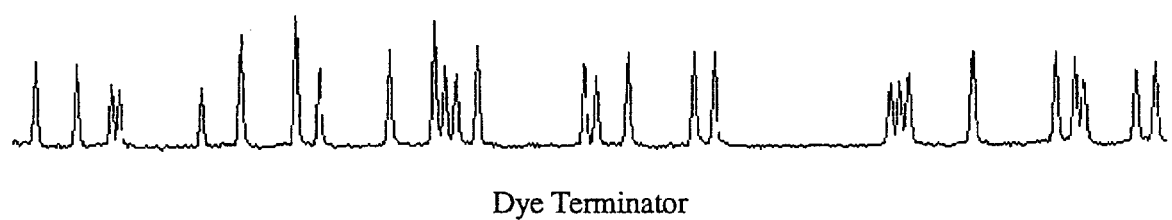
FIG. 1B shows results from a Terminator Titration Assay using 4 pmol of a 6-FAM-ddATP terminator.
Figure 1B:
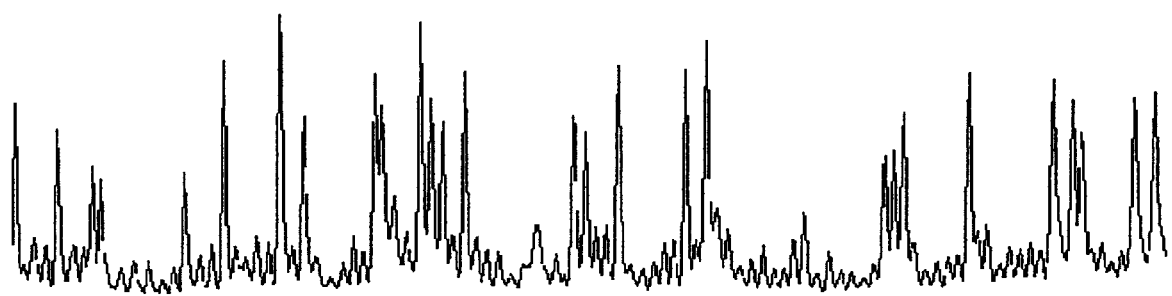
Figure 1C:
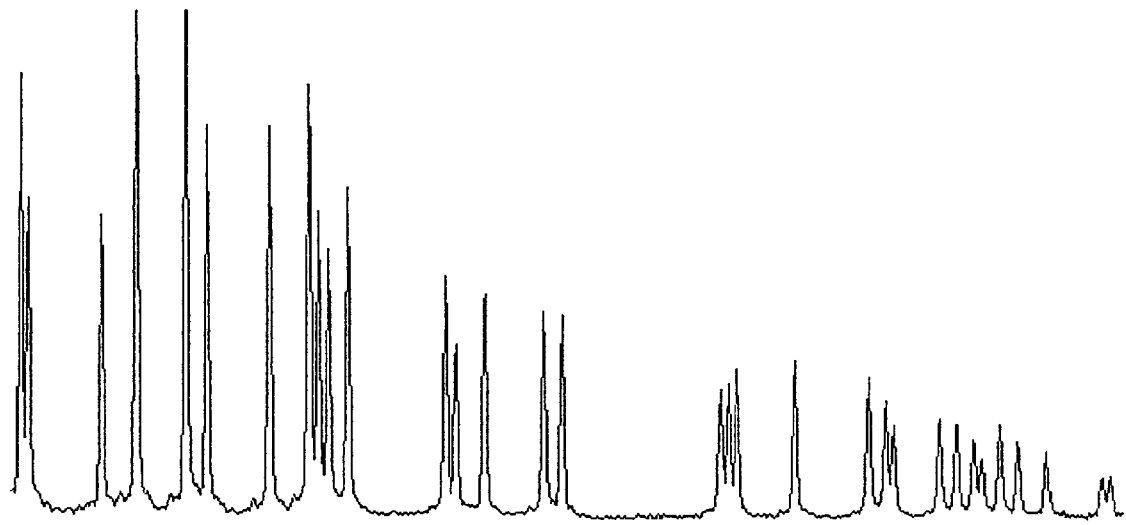
FIG. 1C shows results from a Terminator Titration Assay using 150 pmol of a 6-FAM-ddATP terminator.
Figure 1C:
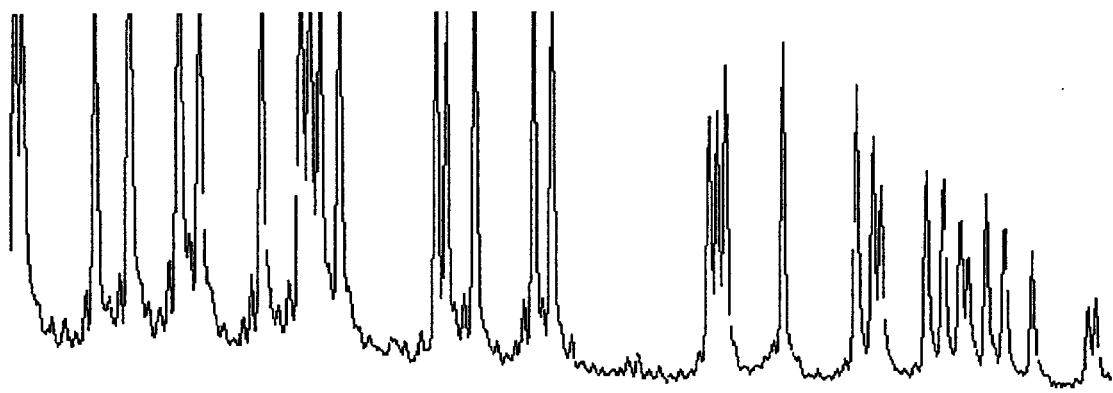
Figure 2:
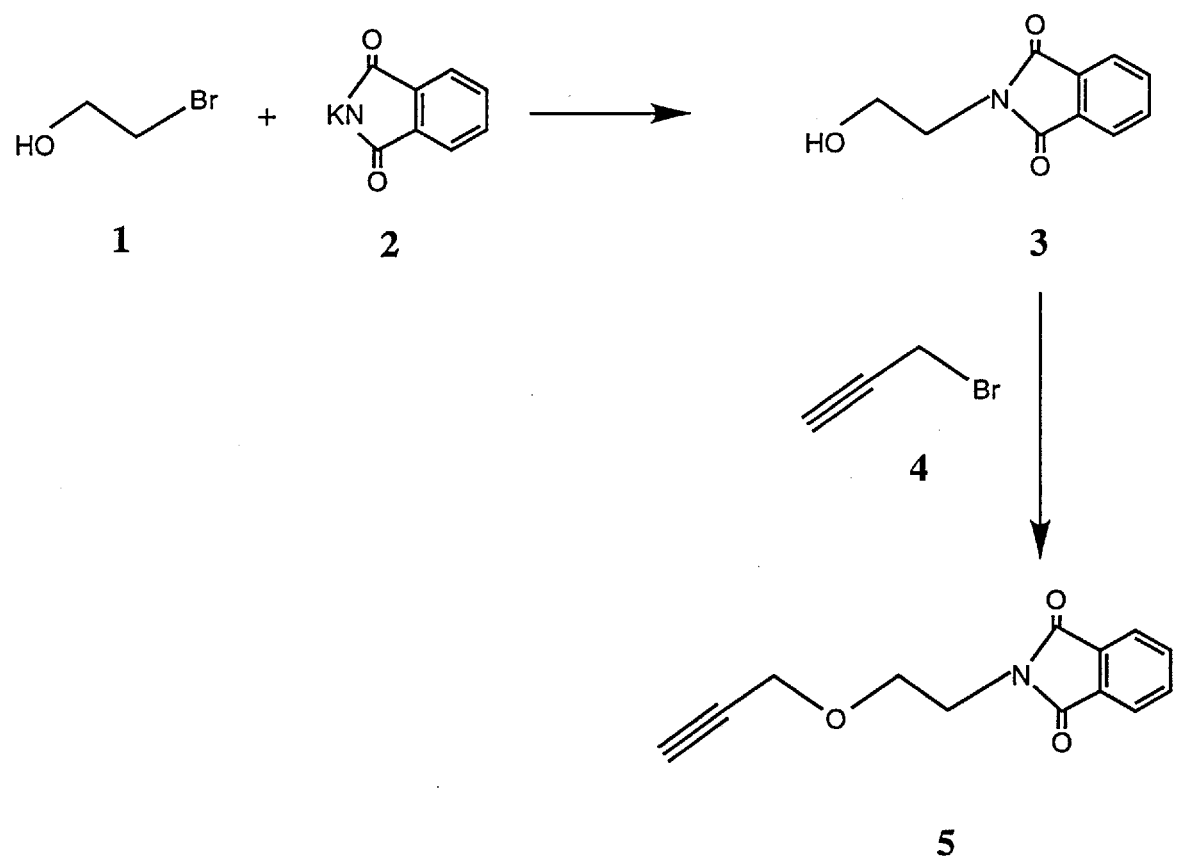
FIG. 2 shows the synthesis of 2-phthalimidoethanol (3) and 3-(2-phthalimidoethoxy)propyne (5).
Figure 3:
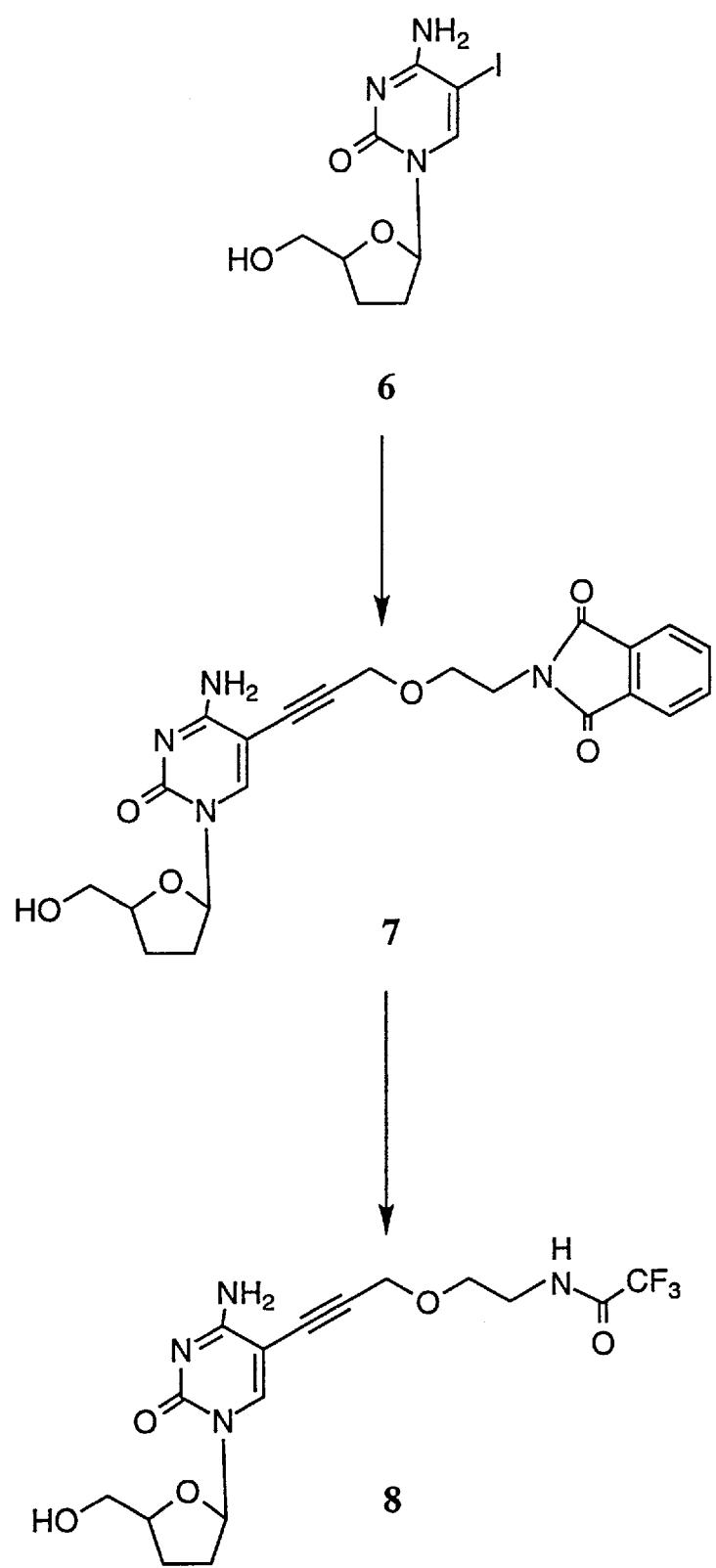
FIG. 3 shows the synthesis of 5-{3-(2-phthalamidoethoxy)-propyn-1-yl}-2',3'-dideoxycytidine (7) and of 5-{3-(2-trifluoroacetamidoethoxy)propyn-1-yl}-2',3'-dideoxycytidine (8).
Figure 4:
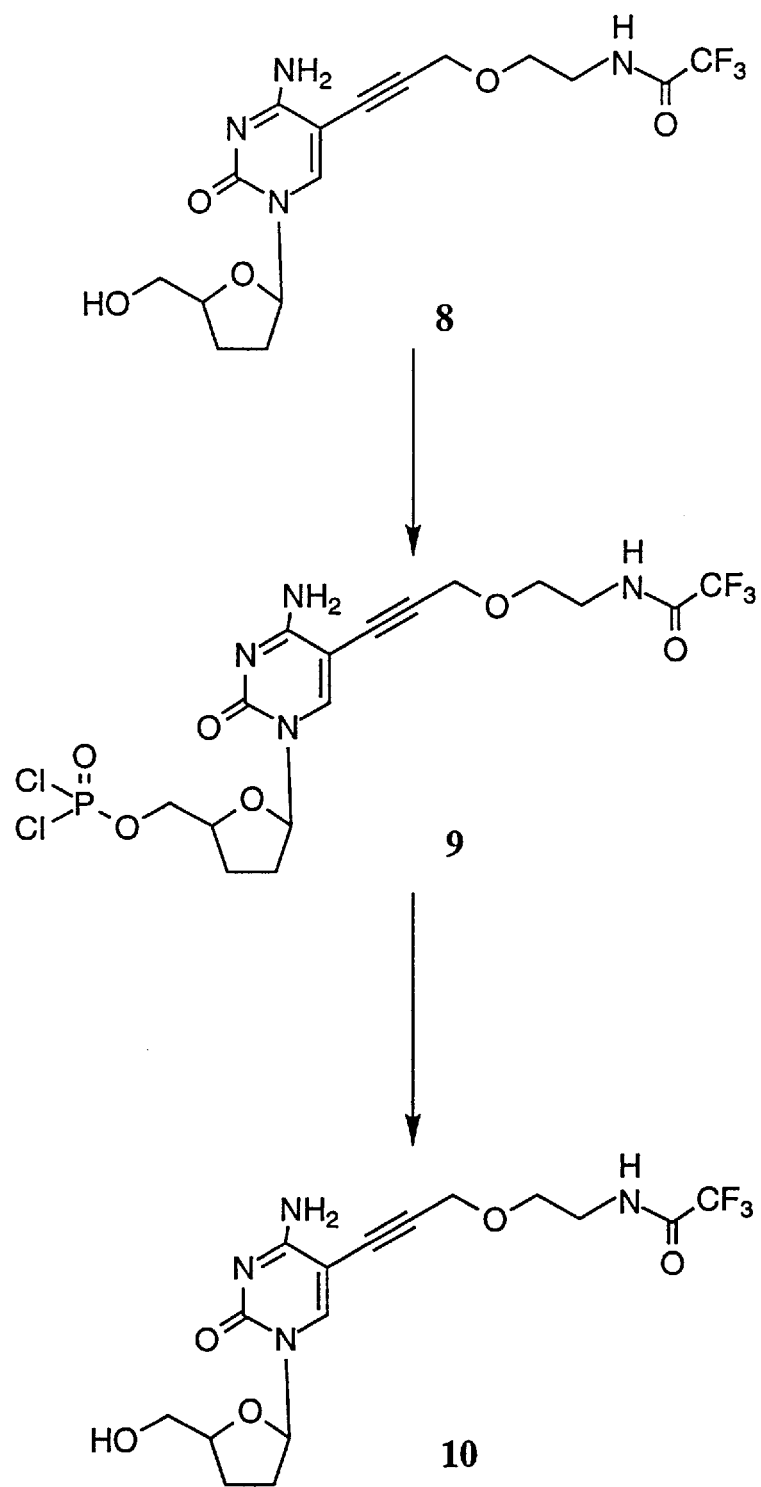
FIG. 4 shows the synthesis of 5-{3-(2'-trifluoroacetamidoethoxy)propyn-1-yl}-2',3'-dideoxycytidine monophosphate (10).
Figure 5:
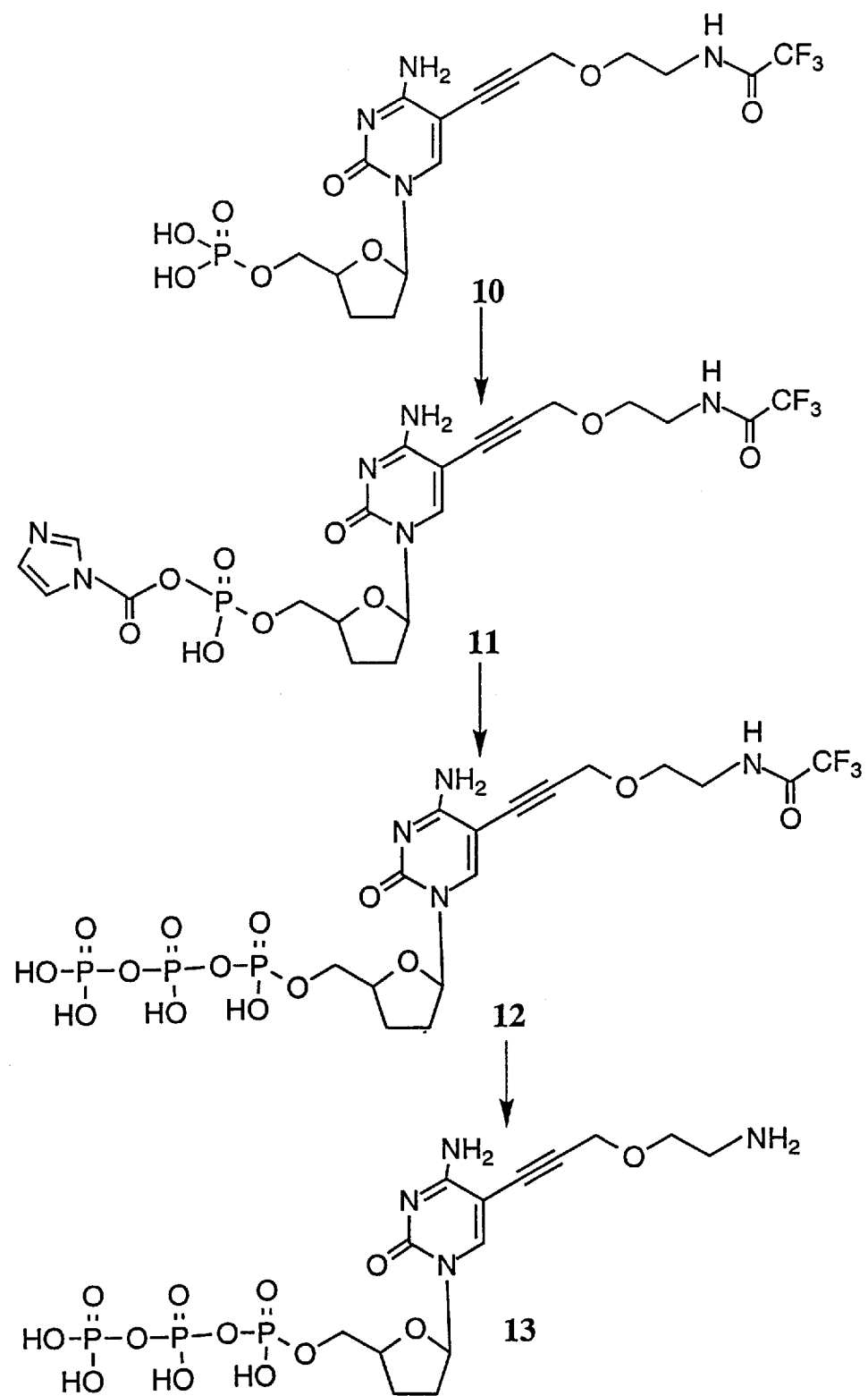
FIG. 5 shows the synthesis of 5-{3-(2-trifluoroacetamidoethoxy)propyn-1-yl}-2',3'-dideoxycytidine triphosphate (12) and 5-{3 -(2-aminoethoxy)propyn-1-yl}-2',3'-dideoxycytidine triphosphate (13).
Figure 6:
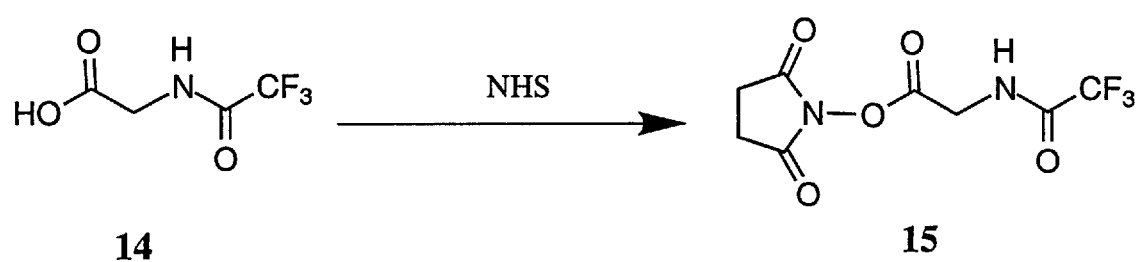
FIG. 6A shows the synthesis of trifluoroacetamidoglycine NHS ester (15).
FIG. 6B shows the synthesis of 4-(trifluoroacetamidomethyl) benzoate NHS ester (18).
FIG. 6C shows the synthesis of trifluoroacetamidobut-2-ynoic NHS ester (21).
Figure 6:
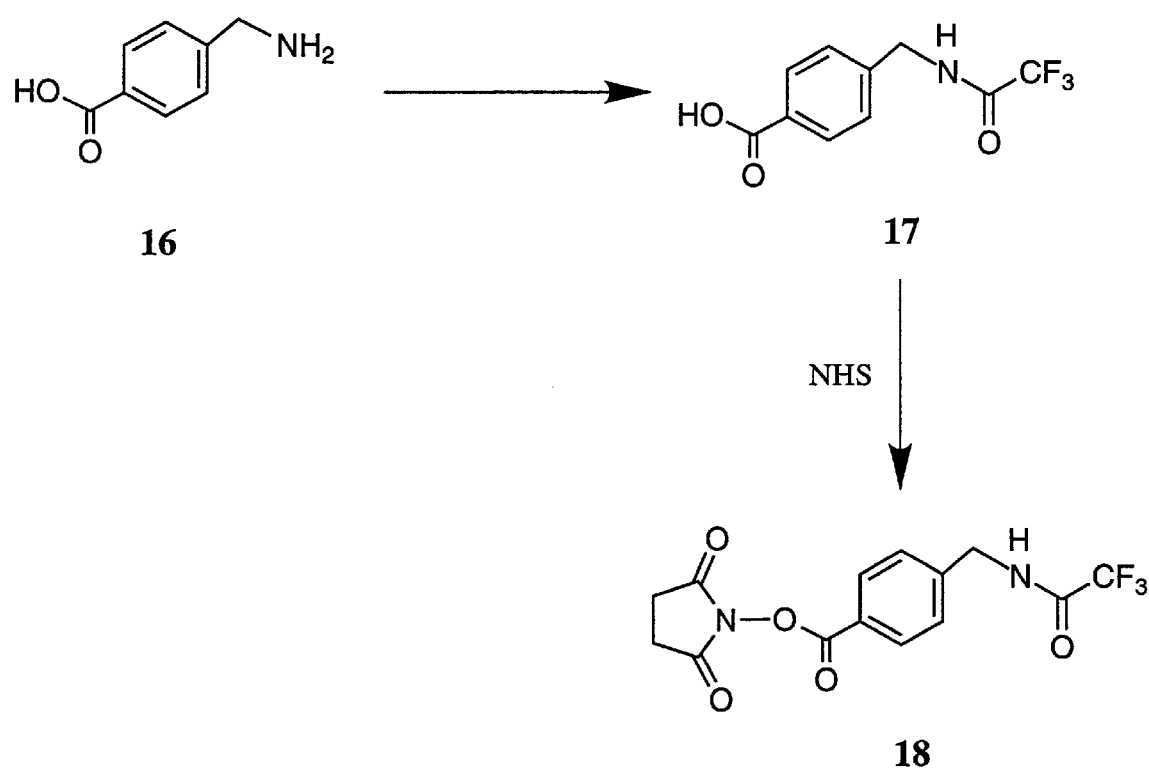
Figure 6:
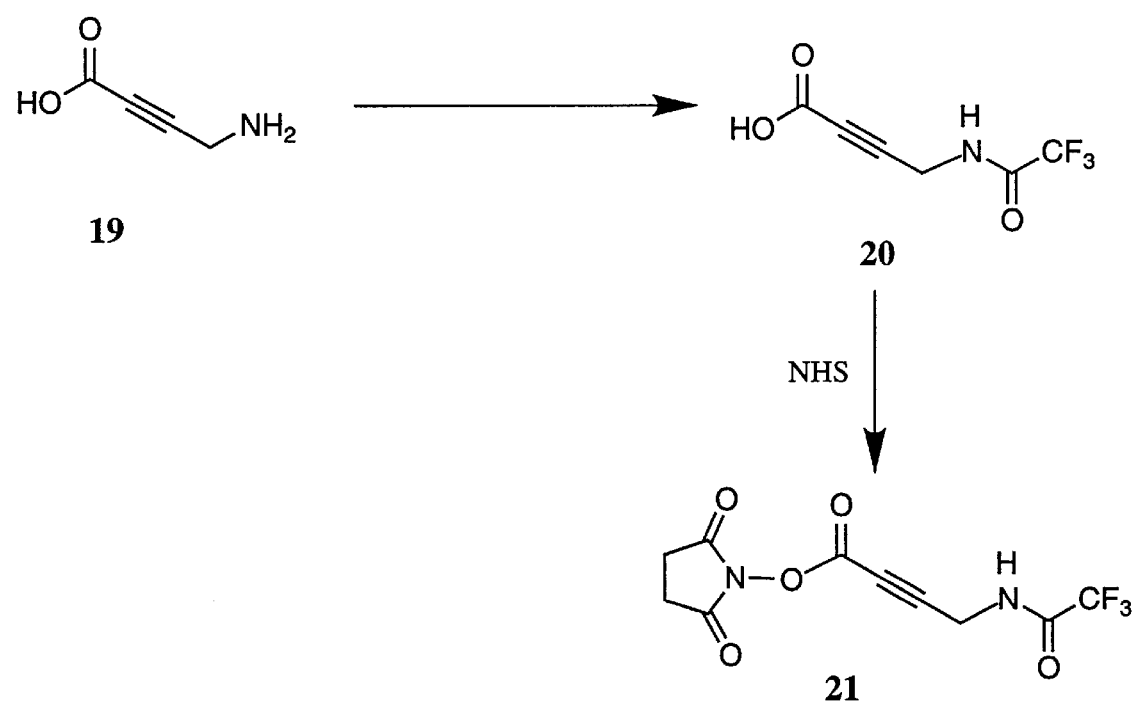
Figure 7:
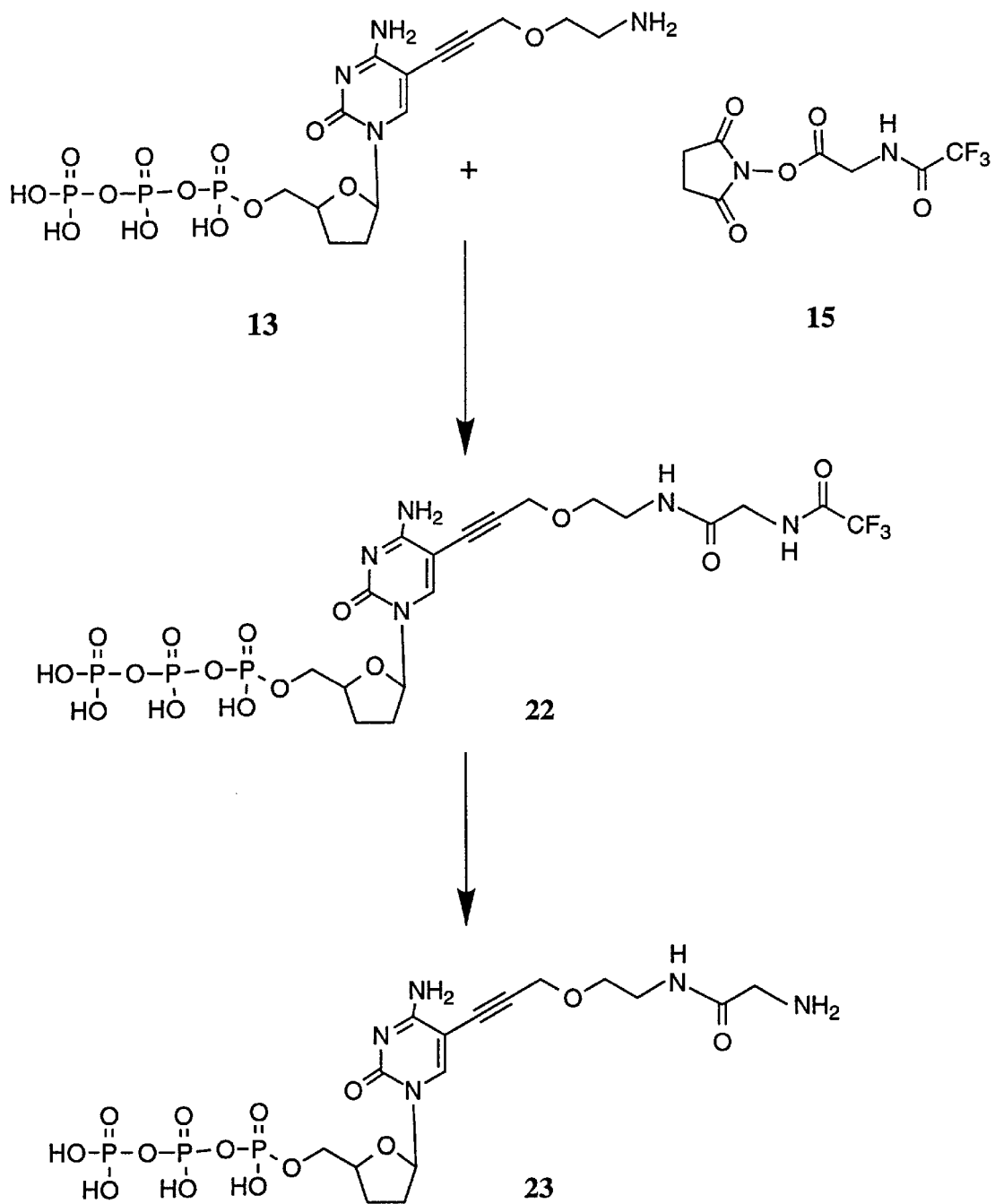
FIG. 7 shows the synthesis of 5-[3-{2-[N-(2-aminoacetyl)]aminoethoxy}propyn-1-yl]-2',3'-dideoxycytidine triphosphate (23).
Figure 8:
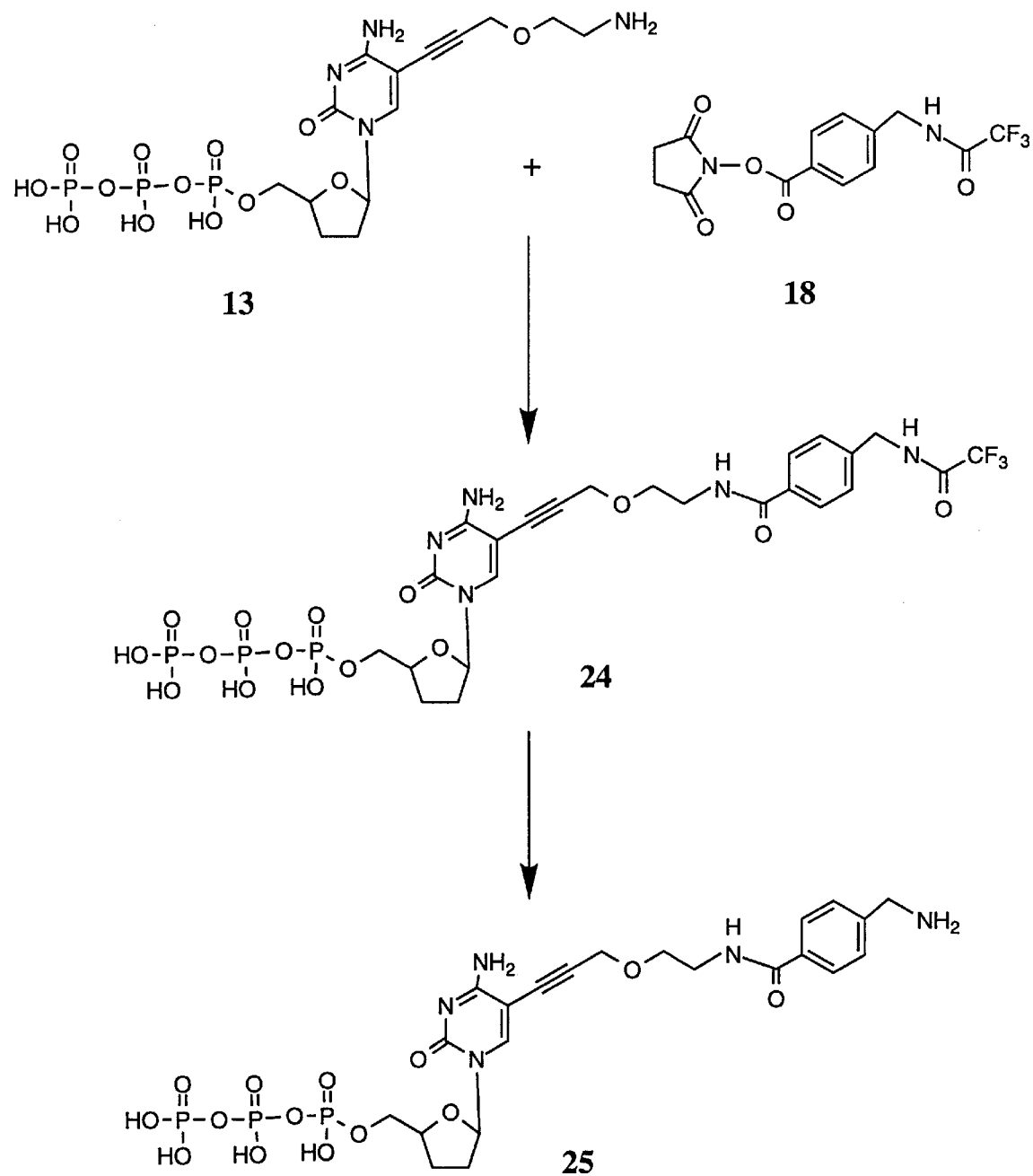
FIG. 8 shows the synthesis of 5-[3-{2-[N-(4-aminomethyl benzoyl)]amino ethoxy}propyn-1-yl]-2',3'-dideoxycytidine triphosphate (25).
Figure 9:
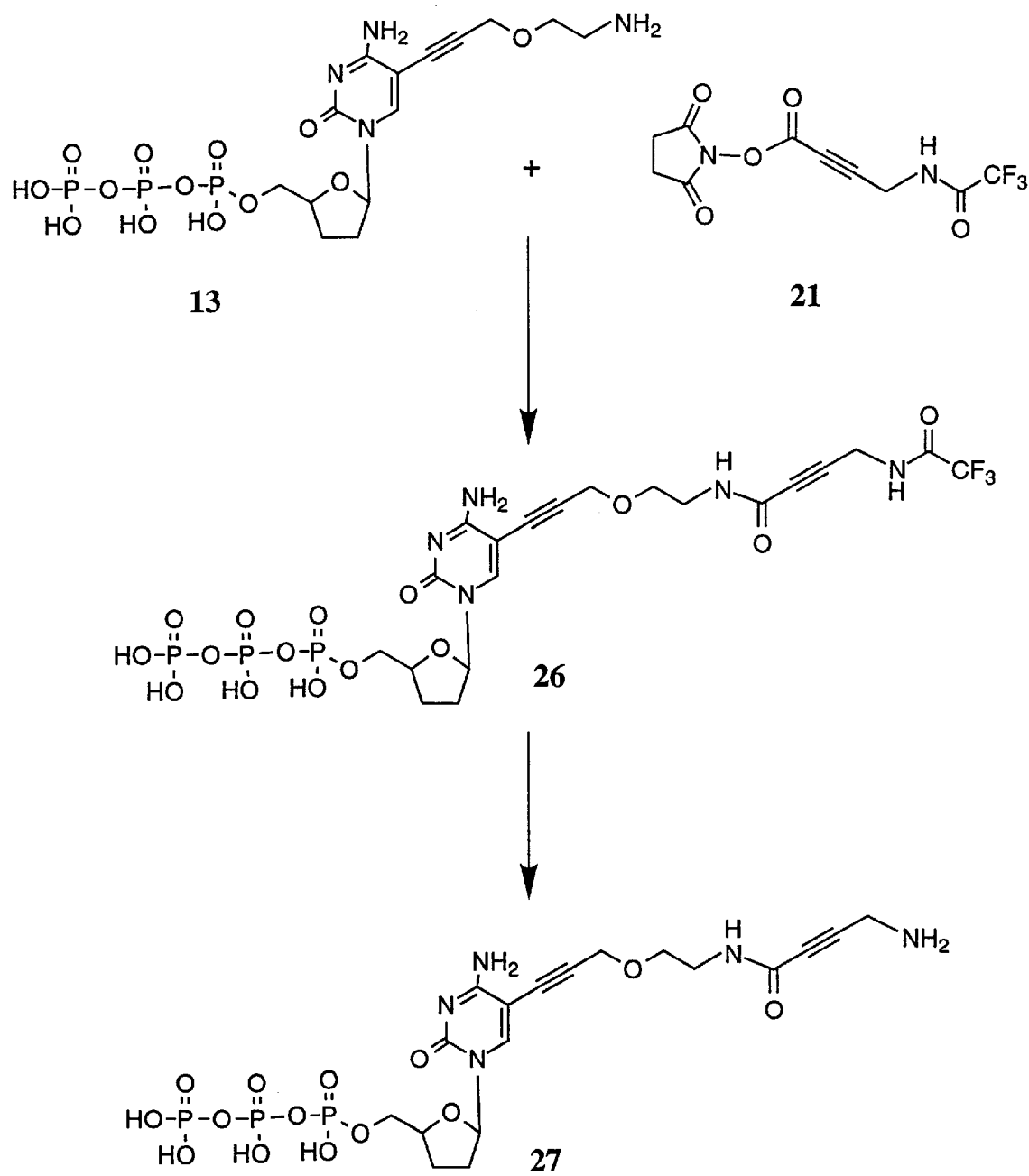
FIG. 9 shows the synthesis of 5-[3-{2-[N-(2-amino-but-2-ynoic)]aminoethoxy}propyn-1-yl]-2',3'-dideoxycytidine triphosphate (27).

FIGS. 1A–C show typical results from a Terminator Titration Assay where the primer was labeled with TAMRA dye, and a ddATP terminator was labeled with 6-FAM dye where a traditional propargylamido linker was used for linking the TAMRA dye to the dideoxynucleotide terminator. The traces show fluorescence intensity at a given wavelength as a function of time during an electrophoresis run for nucleotides 71–175. The amount of dye-terminator added to the primer extension reaction was variable: in FIG. 1A 1 pmol terminator was used, in FIG. 1B 4 pmol terminator was used, and in FIG. 1C 150 pmol terminator was used. The top trace in each panel is fluorescence emitted by the dye-labeled terminator and collected at 535–545 nm and the bottom trace in each panel is fluorescence emitted from the dye-labeled primer and collected at 575–585 nm. The dye primer trace (bottom) shows false stops, i.e., fragments not terminating in a dye-labeled terminator, as well as properly terminated fragments. The dye terminator trace (top) shows the specific incorporation of the dye-labeled terminator.

FIG. 1A shows data for a reaction using 1 pmol of the 6-FAM-ddATP terminator. Very little specific incorporation was detected as evidenced by the small peaks in the dye terminator trace. The false stops shown in the dye-primer trace were essentially as large as any specifically-terminated peaks. This pattern indicates that the dye-terminator concentration was too low. FIG. 1B shows data for a reaction using 4 pmol of the 6-FAM-ddATP terminator. Good specific terminator incorporation was observed in the terminator trace with relatively even peak heights throughout the sequencing ladder. In the dye primer trace, easily distinguishable peaks above the false-stop noise were present, the peaks comigrating with the peaks of the dye terminator trace. This pattern indicates that the dye terminator concentration was within a useable range. FIG. 1C shows data for a reaction using 150 pmol of the 6-FAM-ddATP terminator. A "top heavy" pattern was seen where the early peaks in the dye terminator trace indicated very high levels of dye terminator incorporation and the later peaks indicated much lower levels of incorporation. This pattern indicates that the dye-terminator concentration was too high.

EXAMPLE 2

Amount of HEX-1-Labeled C-Terminator Required to Form a Full Sequencing Ladder as a Function of Linker Type The table below shows the relative molar excess of dye-labeled C-terminator required to form a full sequencing ladder according to the Terminator Titration Assay as described above in Example 1. The relative molar excess is defined such that the amount of unlabeled dideoxy terminator required to form a full sequencing ladder results in a value of 1. In each case a C-terminator was linked to a HEX-1 dye.

| Linker Arm | [a]Relative Molar Excess Terminator Required |
|---|---|
| None-Unlabeled terminator | 1 |
| Propargylamido | 25 |
| Propargylethoxyamido | 12.1 |
| Substituted-propargylethoxyamido nucleotide: X is glycine | 62.5 |
| Substituted propargylethoxyamido nucleotide: X is alkylamino benzoic acid (para conformation) | 6.25 |

[a]The relative molar excess is defined such that the amount of unlabeled dideoxy terminator required to form a full sequencing ladder results in a value of 1.0.

EXAMPLE 3

Synthesis of 5-{3-(2-Aminoethoxy)propyn-1-yl}-2',3'-dideoxycytidine Triphosphate (13)

A. Materials and Methods

Thin layer chromatography (TLC) was conducted on glass plates precoated with 250 μm layers of silica gel 60-$F_{25}$4 Compounds were located on the TLC plate after developing by quenching of fluorescence and/or by charring with 5% sulfuric acid. Flash column chromatography was performed on SIP brand silica gel 60 Å, 230–400 Mesh ASTM (Baxter Scientific p/n C4582-87). NMR spectra were obtained as follows: $^1$H NMR spectra were recorded at 300 MHz on solutions dissolved in $CDCl_3$ (internal $Me_4Si$, δ0) or $D_2O$ (external $Me_4Si$, δ0) at ambient temperature; $^{13}$C NMR spectra were recorded at 75.5 MHz on solutions dissolved in $CDCl_3$ (internal $Me_4Si$, δ0); $^{19}$F NMR spectra were recorded at 282.23 MHz on solutions in $CDCl_3$ or $D_2O$ (external $CFCl_3$, δ0); and $^{31}$P NMR spectra were recorded at 121.44 MHz on solutions in $D_2O$. In all cases, NMR data were in accord with the proposed structures. Unless otherwise indicated, all reactions were carried out at ambient temperature, and in the work-up, solutions in organic solvents were washed with equal volumes of aqueous solutions. Organic solutions were generally dried over anhydrous $Na_2SO_4$ prior to concentration on a rotary evaporator under vacuum with a bath temperature of 40°–50° C. The HPLC systems used for analytical and preparative purposes were as follows:

Analytical reverse-phase HPLC: column: Spheri-5 RP-C 18, 5 μm particle size, 220×4.6 mm (PE Applied Biosystems p/n 0711-0017); gradient: 0 to 50% acetonitrile at 1.5. ml/min over 20 min, followed by 50% acetonitrile to 100% acetonitrile at 1.5 ml/min over 10 min.

Analytical ion pair HPLC: column: Aquapore™ OD-300, 7 μm particle size, 220×4.6 mm (PE Applied Biosystems p/n 0711-0331); gradient: 0 to 40% acetonitrile at 1.5 ml/min over 30 min, followed by 40% acetonitrile to 60% acetonitrile at 1.5 ml/min over 5 min.

Preparative anion exchange HPLC: column: Aquapore™ Anion, 20 μm particle size, 250×10 mm (PE Applied Biosystems p/n 0711-0172); gradient: 40% acetonitrile:60% 100 mM TEAB, pH 7.0 to 40% acetonitrile:60% 1.5 mM TEAB pH 8 at 4.5 ml/min over 20 min, followed by isocratic elution.

Preparative reverse phase HPLC: column: Prep Nova Pak HR-C18, 6 μm particle size, 60 Å pore size, 300×40 mm (Waters Division of the Millipore Corporation p/n WAT037704); gradient (for mono and triphosphates): 100% 100 mM TEAB pH 7 to 20% acetonitrile:80% 100 mM TEAB pH 7 at 50 ml/min over 30 min, followed by 20% acetonitrile:80% 100 mM TEAB pH 7 to 50% acetonitrile:50% 100 mM TEAB pH 7 over 10 min; gradient (for dye-labeled triphosphates): 100% 100 mM TEAB pH 7 to 10% 100 mM TEAB pH 7: 90% acetonitrile.

B. Synthesis of 2-Phthalimidoethanol (3)

Potassium phthalimide 2 (2.7 g, 14.6 mmol) was added to a solution of bromoethanol 1 in N,N-dimethylformamide (12 mL, 14.1 mmol). After stirring for 12 h at 70° C., the mixture was concentrated and then diluted with dichloromethane (100 mL). After removal of solids by filtration, the organic layer was washed with water, dried, and concentrated. The concentrate was purified by flash column chromatography (3:2 to 2:3 hexane-ethyl acetate) to give compound 3 as a white solid (1.19 g, 44.12%) having a $R_F$ of 0.22 (3:2 hexane-ethyl acetate). See FIG. 2.

C. Synthesis of 3-(2-Phthalimidoethoxy)propyne (5)

To a stirred solution of compound 3 (1.14 g, 5.96 mmol) in N,N-dimethylformamide (20 mL) was added NaH (0.36 g, 80%) dropwise. After complete NaH addition, stirring was continued for 0.5 h at room temperature, and the reaction was cooled to 0° C. Propargyl bromide 4 (1.5 mL, 13.47 mmol) was added, and the stirring was continued for an additional 0.5 h at 0° C., then, at room temperature for 2 h. After careful addition of methanol to decompose excess NaH, the solvent was evaporated and the crude product was purified by flash column chromatography (3:2 to 1:1 to 2:3 hexane-ethyl acetate) to give compound 5 as a solid (495 mg, 36.2%) having an $R_F$ of 0.22 (3:2 hexane-ethyl acetate). See FIG. 2.

D. Synthesis of 5-{3-(2-Phthalamidoethoxy)-propyn-1-yl}-2',3'-dideoxycytidine (7)

5-iodo-2',3'-dideoxycytidine 6 (100 mg, 0.3 mmol) was reacted with compound 5 (158 mg, 0.69 mmol) in the presence of cuprous iodide (11.4 mg, 0.06 mmol), tetrakis (triphenylphosphine)palladium (69 mg, 0.06 mmol), and triethylamine (84 μL, 0.6 mmol) in N,N-dimethylformamide (1 mL) for 12 h at room temperature under Argon atmosphere. The reaction was then diluted with 2 g bicarbonate form of Dowex-1 anion exchange resin in methanol. After stirring for 1 h at room temperature the reaction mixture was filtered and concentrated. The product was purified by flash column chromatography (13:1 dichloromethene-methanol) to give compound 7 (75 mg, 57.66%) having an $R_F$ of 0.23 (solvent 9:1 dichloromethane-methanol). See FIG. 3.

E. Synthesis of 5-{3-(2-Trifluoroacetamidoethoxy)propyn-1-yl}-2',3'-dideoxycytidine (8)

A mixture of compound 7 (73 mg, 0.17 mmol) and ethylenediamine (400 µL) was heated at 80° C. in ethanol (4 mL) for 1 h. The reaction was then evaporated to dryness, the residue was dissolved in N,N-dimethylformamide (2 mL), and methyl trifluoroacetate (6.5 mL) was added. After stirring for 1 h at 80° C., the solvent was evaporated and the residue was purified by flash column chromatography (9:1 dichloromethane-methanol) to give compound 8 (36 mg, 50.7%) having an $R_F$ of 0.24 (solvent 9:1 dichloromethane-methanol). See FIG. 3.

F. Synthesis of 5-{3-(2'-Trifluoroacetamidoethoxy)propyn-1-yl}-2',3'-dideoxycytidine monophosphate (10)

Freshly distilled phosphorous oxychloride (16.2 µL, 0.17 mmol) was added to nucleoside 8 (18.8 mg, 0.046 mmol) in trimethylphosphate (150 µL) at −30° C. to form the corresponding dichloromonophosphate 9. The reaction mixture was allowed to warm to −5° C. over a period of 80 min and stirring was continued for an additional 1 h at room temperature. The reaction was quenched with 2M TEAB buffer pH 8.0, and purified by preparative reverse phase HPLC as described above. Fractions corresponding to product were concentrated to give monophosphate 10 (12.3 mg, 54.56%). See FIG. 4.

G. Synthesis of 5-{3-(2-Trifluoroacetamidoethoxy)propyn-1-yl}-2',3'-dideoxycytidine triphosphate (12)

The monophosphate 10 (7.4 mg, 15.3 mmol) dissolved in N,N-dimethylformamide (200 µl) was stirred with carbonyldimidazole (CDI) (4.2 mg, 25.9 mmol) for 1 h at room temperature. Excess CDI was quenched by the addition of dry methanol (40 µL). The activated monophosphate 11 was stirred with a solution of tributylammonium pyrophosphate in N,N-dimethylformamide (160 µL) containing n-tributylamine (16 µL) for 24 h at room temperature. The reaction was quenched with 2M TEAB pH 8.0 and purified by preparative reverse phase HPLC as described above. The fractions corresponding to product were concentrated to give triphosphate 12. See FIG. 5.

H. Synthesis of 5-{3-(2-Aminoethoxy)propyn-1yl}-2',3'-dideoxycytidine triphosphate (13)

The purified protected triphosphate 12 was taken up in concentrated aqueous $NH_4OH$ (4 mL) and stirred for 2.5 h at room temperature. The reaction mixture was concentrated to give the propargylethoxyamido nucleotide 13. The concentrated compound was then formulated as a bulk with 0.1M TEAB pH 7.0 to a concentration of 2.6 mM. The concentration and purity of the formulated bulk were confirmed by UV/Vis spectroscopy and analytical ion pair HPLC as described above, respectively. See FIG. 5.

EXAMPLE 4

Synthesis of 5-[3-{2-[N-(2-aminoacetyl)]aminoethoxy}propyn-1-yl]-2',3'-dideoxycytidine Triphosphate (23) [Glycine-Substituted Propargylethoxyamido Nucleotide]

A. Synthesis of trifluoroacetamidoglycine NHS ester (15) —FIG. 6A

Trifluoroacetamidoglycine 14 (0.96 g, 5.6 mmoles) was reacted with N-hydroxysuccinimide (0.65 g, 5.7 mmoles) and 1-(3-dimethylaminopropyl)-3-ethylcarbodiimide methiodide (1.68 g, 5.7 mmoles) in dry DMF (10 mL) for 1 hour at room temperature. The reaction solution was diluted with ethyl acetate (200 mL) and washed with 0.1N HCl (2×100 mL). The ethyl acetate extract was then dried over sodium sulfate and concentrated to give the trifluoroacetamidoglycine NHS ester 15 (1.43 g, 100%).

B. Synthesis of 5-[3-{2-[N-(2-aminoacetyl)]aminoethoxy}propyn-1-yl]-2',3'-dideoxycytidine triphosphate (23)—FIG. 7

The propargyethoxyamido nucleotide 13 (200 µl, 15.2 mM) in 100 mM TEA-bicarbonate (pH 7.0) was evaporated to dryness. It was then resuspended in 100 µl of a 250 mM bicarbonate buffer (pH 9.0). A solution of the trifluoroacetamidoglycine NHS ester 15 (50 µl, 23% w/w in DMSO) was added and stirred overnight at room temperature. The reaction mixture was then purified by preparative reverse phase HPLC (C-18 reverse phase) as follows: column: Aquapore ODS, 20 µm particle size, 250×10 mm (PE Applied Biosystems p/n 0711-0163); gradient: 0 to 50% acetonitrile at 4.5 ml/min over 20 min, followed by 40% acetonitrile to 100% acetonitrile at 4.5 ml/min over 10 min. The fractions corresponding to product were pooled and diluted with equal volumes of 100 mM TEA-bicarbonate (pH 7.0) then concentrated in vacuo to give the purified protected triphosphate 22.

The purified protected triphosphate 22 was taken up in concentrated aqueous $NH_4OH$ (2 mL) and stirred overnight at room temperature. The reaction mixture was concentrated to give the glycine-substituted propargylamino nucleotide 23. A bulk solution of the glycine-substituted propargylamino nucleotide 23 was formulated by dissolution of the reaction mixture in 0.1M TEAB pH 7.0 to a concentration of 4.84 mM. The concentration and purity of the formulated bulk solution were confirmed by UV/Vis spectroscopy and analytical reverse phase HPLC as describe above in Example 3.

EXAMPLE 5

Synthesis of 5-[3-{2-[N-(4-aminomethyl benzoyl)]aminoethoxy}propyn-1-yl]-2',3'-dideoxycytidine Triphosphate (25) [Methylamino-benzoic-acid (para)-substituted Propargylethoxyamido Nucleotide]

A. Synthesis of 4-(trifluoroacetamidomethyl) benzoate NHS ester (18)—FIG. 6B 4-amino methyl benzoic acid 16 (4 g, 26.5 mmol) was dissolved in DMSO (60 mL) and methyl trifluoroacetate (3 mL) and triethylamine (3 mL) were added to the solution. After stirring for 5 h at 60° C. the reaction solution was diluted with ethyl acetate (500 mL) and washed with water (6×200 mL). The ethyl acetate extract was then dried over sodium sulfate and concentrated to give the trifluoroacetamidomethyl benzoic acid 17 (4.6 g, 70.3%) as a white solid.

The trifluoroacetamidomethyl benzoic acid 17 (4.49 g, 18.2 mmol) was reacted with N-hydroxysuccinimide (2.09 g, 18.2 mmol) and 1,3-dicyclohexyl-carbodiimide (3.74 g, 18.2 mmol) in 100 ml ethyl acetate for 2 h at room temperature. The reaction solution was filtered to remove a white precipitate and the organic layer was washed with 1N HCl (100 mL). The ethyl acetate extract was then dried over sodium sulfate and concentrated. The concentrate was chromatographed by normal-phase column chromatography using a silica gel stationary phase with the following step gradient: 40:1 dichloromethane:ethylacetate followed by 10:1 dichloromethane:ethyl acetate to give the 4-(trifluoroacetamidomethyl) benzoate NHS ester 18 as a white solid (3.5 g, 56%).

B. Synthesis of 5-[3-{2-[N-(4-aminomethyl benzoyl)] aminoethoxy}propyn-1-yl]-2'.3'-dideoxycytidine triphosphate (25)—FIG. 8

The propargylethoxyamido nucleoside 13 (200 µl, 15.2 mM) in 100 mM TEA-bicarbonate (pH 7.0) was evaporated to dryness. It was then resuspended in 150 µl of a 250 mM bicarbonate buffer (pH 9.0). A solution of the 4-(trifluoroacetamidomethyl) benzoate NHS ester 18 (100 µl, 25 mg in 100 µl DMSO) was added and stirred overnight at room temperature. The reaction mixture was purified by preparative reverse phase HPLC as described above in Example 4. The fractions corresponding to product were pooled and diluted with an equal volume of 100 mM TEA-bicarbonate (pH 7.0) then concentrated in vacuo to give the purified protected triphosphate 22.

The purified protected triphosphate 22 was taken up in concentrated aqueous $NH_4OH$ (2 mL) and stirred overnight at room temperature. The reaction mixture was concentrated to give the methylamino-benzoic-acid (para)-substituted propargylamino nucleotide 25. A bulk solution of the substituted propargylamino nucleotide 25 was formulated by dissolution of the reaction mixture in 0.1M TEAB pH 7.0. The concentration and purity of the formulated bulk solution were confirmed by UV/Vis spectroscopy and analytical reverse phase HPLC as describe above in Example 3.

EXAMPLE 6

Attachment of Dye to a Substituted Propargylethoxyamido Nucleotide

The substituted propargylethoxyamido nucleotide in 100 mM TEA-bicarbonate (pH 7.0) was evaporated to dryness. It was then resuspended in 250 mM bicarbonate buffer (pH 9.0). A solution of a desired dye-NHS (in DMSO) was added and stirred in the dark overnight at room temperature. The reaction mixture was purified by preparative anion exchange HPLC as described above. The fractions corresponding to product were concentrated and repurified by preparative reverse phase HPLC as described above. Final product was dried in vacuo and diluted with 50 mM CAPSO, pH 9.6, to a concentration of 1 mM. The concentration and purity of the formulated bulk was confirmed by UV/VIS spectroscopy and analytical ion-pairing HPLC as described above, respectively.

EXAMPLE 7

Figure 10:
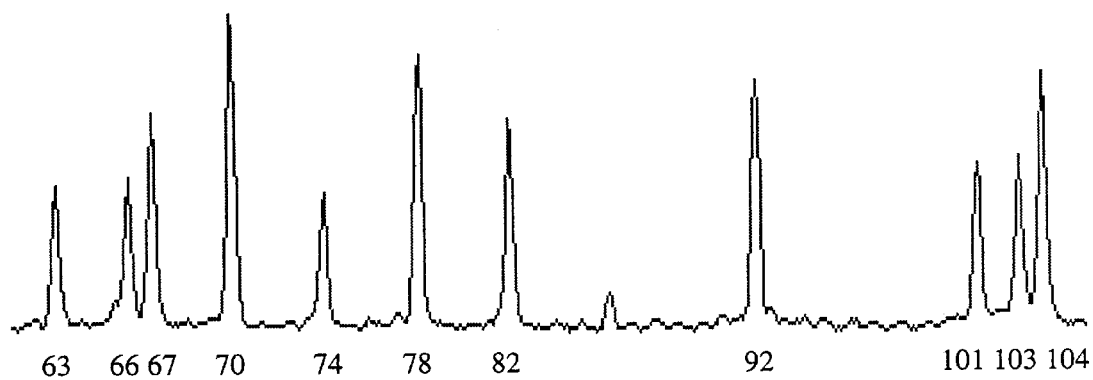
FIG. 10 shows results from three different dye-terminator sequencing reactions where each reaction utilized a different linker for linking a dye to a terminator.
Figure 10:
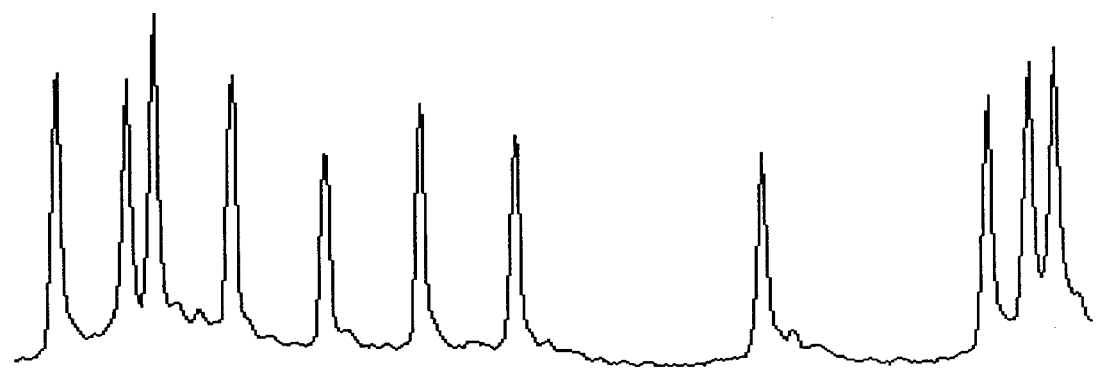
Figure 10:
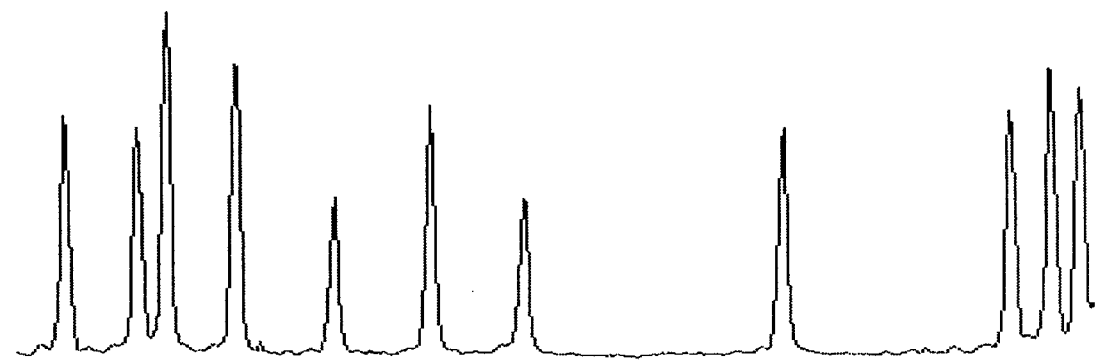

Improved Peak Height Evenness Using the Substituted Propargylethoxyamido Dideoxynucleotides of the Invention FIG. 10 shows an electropherogram of single color sequencing reactions using HEX-1-labeled ddCTP where the HEX-1 dye is attached to a terminator using each of three different types of linkers. The optimum terminator concentration was used for each linker type based on the above described Terminator Titration Assay. The top panel shows results using a propargylethoxyamido linker at 50 µm, the middle panel shows results using a methylamino-benzoic-acid-(para)-substituted propargylethoxyamido linker at 25 µm, and the bottom panel shows results using a glycine-substituted propargylethoxyamido linker at 250 µm. As indicated by the numbers under the top electropherogram in FIG. 10, the portion of the sequencing ladder shown in FIG. 10 runs from base 63 to base 104 of the sequence of pGEM-3Zf(+) using the −21 M13 sequencing primer (forward). The relative error for each of the experiments were as follows, where as used herein the term "relative error" means the ratio of standard deviation in peak height and mean peak height across the portion of the electropherogram shown in the figure.

| Linker Type | Relative Error |
| --- | --- |
| Propargylethoxyamido | 0.341 |
| Methylamino-benzoic-acid-(para)-substituted propargylethoxyamido | 0.141 |
| Glycine-substituted propargylethoxyamido | 0.310 |

All publications and patent applications are herein incorporated by reference to the same extent as if each individual publication or patent application was specifically and individually indicated to be incorporated by reference.

Although only a few embodiments have been described in detail above, those having ordinary skill in the chemical arts will clearly understand that many modifications are possible in the preferred embodiment without departing from the teachings thereof All such modifications are intended to be encompassed within the following claims.

We claim:

1. A polynucleotide comprising a nucleotide compound having the structure:

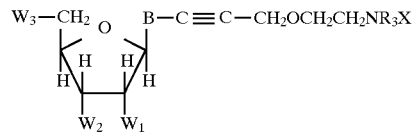

wherein:

X is selected from the group consisting of

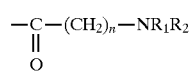

where n ranges from 1 to 5,

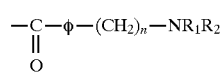

where n ranges from 1 to 5,

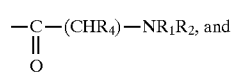

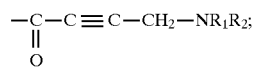

$R_1$ and $R_2$ taken separately are selected from the group consisting of —H, lower alkyl, protecting group, and label;

$R_3$ is selected from the group consisting of —H and lower alkyl;

B is a 7-deazapurine, purine, or pyrimidine nucleoside base;

wherein when B is purine or 7-deazapurine, the sugar moiety is attached at the $N^9$-position of the purine or deazapurine, and when B is pyrimidine, the sugar moiety is attached at the $N^1$-position of the pyrimidine; and wherein when B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine;

$W_1$ is selected from the group consisting of —H and —OH;

$W_2$ is —OH or a moiety which renders the nucleoside incapable of forming a phosphodiester bond at the 3'-position; and $W_3$ is selected from the group consisting of —PO$_4$, phosphate analog, and —OH.

2. A nucleoside compound having the structure:

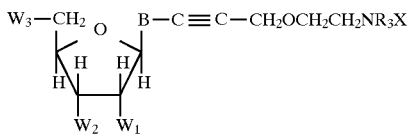

wherein:

X is selected from the group consisting of

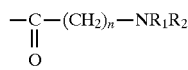

where n ranges from 1 to 5,

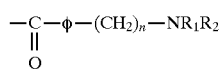

where n ranges from 1 to 5,

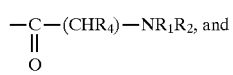

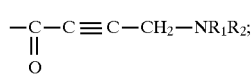

$R_1$ and $R_2$ taken separately are selected from the group consisting of —H, lower alkyl, protecting group, and label;

$R_3$ is selected from the group consisting of —H and lower alkyl;

B is a 7-deazapurine, purine, or pyrimidine nucleoside base;

wherein when B is purine or 7-deazapurine, the sugar moiety is attached at the $N^9$-position of the purine or deazapurine, and when B is pyrimidine, the sugar moiety is attached at the $N^1$-position of the pyrimidine; and wherein when B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine;

$W_1$ is selected from the group consisting of —H and —OH;

$W_2$ is —OH or a moiety which renders the nucleoside incapable of forming a phosphodiester bond at the 3'-position; and $W_3$ is selected from the group consisting of —PO$_4$, —P$_2$O$_7$, —P$_3$O$_{10}$, phosphate analog, and —OH.

3. The nucleoside compound of claim 2 wherein one of $R_1$ and $R_2$ is label.

4. The nucleoside compound of claim 3 wherein the label is a fluorescein-type dye.

5. The nucleoside compound of claim 3 wherein the label is selected from a group consisting of a rhodamine-type dye and a FLAN-type dye.

6. The nucleoside compound of claim 2 wherein:

$W_1$ is —H;

$W_2$ is —OH or a moiety which renders the nucleoside incapable of forming a phosphodiester bond at the 3'-position; and $W_3$ is —P$_3$P$_{10}$.

7. The nucleoside compound of claim 2 wherein $W_2$ selected from the group consisting of —OH, —H, azido, amino, halo, and methoxy.

8. The nucleoside compound of claim 2 wherein $W_2$ selected from the group consisting of —H and fluoro.

9. The nucleoside of claim 2 wherein B is selected from the group consisting of uracil, cytosine, 7-deazaadenine, and 7-deazaguanosine.

10. The nucleoside compound of claim 2 wherein X is alkylamino benzoic acid having a para configuration and n=1.

11. A method for performing a primer extension reaction comprising the steps of:

providing a template nucleic acid;

annealing an oligonucleotide primer to a portion of the template nucleic acid; and adding primer-extension reagents to the primer-template hybrid for extending the primer, the primer extension reagents including a nucleoside compound having the structure:

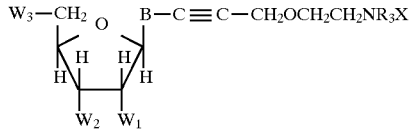

wherein

X is selected from the group consisting of

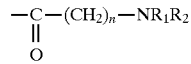

where n ranges from 1 to 5,

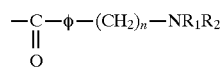

where n ranges from 1 to 5,

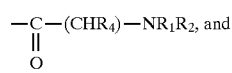

-continued

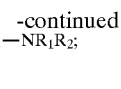

R₁ and R₂ taken separately are selected from the group consisting of —H, lower alkyl, protecting group, and label;

R₃ is selected from the group consisting of —H and lower alkyl;

B is a 7-deazapurine, purine, or pyrimidine nucleoside base;

wherein when B is purine or 7-deazapurine, the sugar moiety is attached at the $N^9$-position of the purine or deazapurine, and when B is pyrimidine, the sugar moiety is attached at the $N^1$-position of the pyrimidine; and wherein when B is a purine, the adjacent triple-bonded carbon is attached to the 8-position of the purine, when B is 7-deazapurine, the adjacent triple-bonded carbon is attached to the 7-position of the 7-deazapurine, and when B is pyrimidine, the adjacent triple-bonded carbon is attached to the 5-position of the pyrimidine;

$W_1$ is selected from the group consisting of —H and —OH;

$W_2$ is —OH or a moiety which renders the nucleoside incapable of forming a phosphodiester bond at the 3'-position; and $W_3$ is selected from the group consisting of —PO₄, —P₂O₇, —P₃$_O$₁₀, phosphate analog, and —OH.

12. The method of claim 11 wherein one of R₁ and R₂ is label and the other is —H.

* * * * *

UNITED STATES PATENT AND TRADEMARK OFFICE
CERTIFICATE OF CORRECTION

PATENT NO.   : 5,770,716  Page 1 of 1
DATED        : June 23, 1998
INVENTOR(S)  : S. Kahn et al.

It is certified that error appears in the above-identified patent and that said Letters Patent is hereby corrected as shown below:

Column 20,
Line 63, and 64: between "$R_3$ is selected from the group consisting of -H and lower and lower alkyl;" and "B is a 7-deazapurine," insert -- $R_4$ is an amino acid side chain, either natural or synthetic; --

Column 21,
Lines 51 and 52: between "$R_3$ is selected from the group consisting of -H and lower alkyl; and B is a 7- deazapurine," insert -- $R_4$ is an amino acid side chain, either natural or synthetic; --

Column 23,
Lines 9 and 10: between "$R_3$ is selected from the group consisting of -H and lower alkyl;" and B is a 7-deazapurine," insert --$R_4$ is an amino acid side chain, either natural or synthetic; --

Signed and Sealed this

Fourteenth Day of August, 2001

*Attest:*

*Attesting Officer*

NICHOLAS P. GODICI
*Acting Director of the United States Patent and Trademark Office*